US008828451B2

(12) United States Patent
Sebti et al.

(10) Patent No.: US 8,828,451 B2
(45) Date of Patent: Sep. 9, 2014

(54) AKT SENSITIZATION OF CANCER CELLS

(75) Inventors: Said M. Sebti, Tampa, FL (US); Jin Q. Cheng, Tampa, FL (US)

(73) Assignee: University of South Florida, Tampa, FL (US)

( * ) Notice: Subject to any disclaimer, the term of this patent is extended or adjusted under 35 U.S.C. 154(b) by 103 days.

(21) Appl. No.: 11/867,394

(22) Filed: Oct. 4, 2007

(65) Prior Publication Data

US 2008/0131526 A1 Jun. 5, 2008

Related U.S. Application Data

(60) Provisional application No. 60/828,154, filed on Oct. 4, 2006.

(51) Int. Cl.
*A61K 33/24* (2006.01)
*A01N 55/02* (2006.01)
*A61K 31/555* (2006.01)

(52) U.S. Cl.
USPC .......................................... 424/649; 514/184

(58) Field of Classification Search
None
See application file for complete search history.

(56) References Cited

U.S. PATENT DOCUMENTS

| 6,150,398 A * | 11/2000 | Vande Woude et al. ...... 514/449 |
| 2004/0038322 A1* | 2/2004 | Collins et al. .................. 435/7.23 |
| 2004/0102360 A1* | 5/2004 | Barnett et al. ..................... 514/1 |
| 2006/0030536 A1* | 2/2006 | Yu et al. ............................ 514/44 |
| 2006/0247188 A1* | 11/2006 | Cheng et al. ..................... 514/43 |

FOREIGN PATENT DOCUMENTS

WO 2005094322 A2 10/2005

OTHER PUBLICATIONS

Goldman et al [Editors] "Chapter 198: Principles of Cancer Therapy." Cecil's Textbook of Medicine (Twenty-First Edition, vol. 1). W.B. Saunders Company, 2000. pp. 1060-1074.*
Kim et al. AKT/PKB signaling mechanisms in cancer and chemoresistance. Frontiers in Bioscience, 10, 975-978, Jan. 1, 2005.*
Yang et al. Akt/protein kinase B signaling inhibitor-2, a selective small molecule inhibitor of aAkt signaling with antitumor activity in cancer cells overexpressing Akt. Cancer Research, 64, 4394-4399, Jul. 1, 2004.*
Rosenberg. Fundamental Studies with Cisplatin. Charles F. Kettering Prize. 1984 General Motors Cancer Research Foundation Prizewinners Laureates Lectures, Jack Masur Auditorium, National Institutes of Health, Bethesda, Maryland, Jun. 13, 1984.*
Naykern et al. Synergistic induction of apoptosis in human leukemia T cells by the Akt inhbiitor perifosine and etoposide through activation of intrinsic and Fas-mediated extrinsic cell death pathways. (Mol. Cancer Therp. 2006; 5: 1559-1570, published online Jul. 3, 2006).*

Rajski et al. DNA cross-linking agents as antitumor drugs. Chem. Rev. 1998, 98, 2723-2795.*
Shi et al. Optimal classes of chemotherapeutic agents sensitized by specific small-molecule inhibitors of Akt in vitro and in vivo. Neoplasia. vol. 7, No. 11, Nov. 2005, pp. 992-1000.*
Alsina M., et al., Farnesyltransferase inhibitor tipifarnib is well tolerated, induces stabilization of disease, and inhibits farnesylation and oncogenic/tumor survival pathways in patients with advanced multiple myeloma. *Blood* 2004; 103: 9: 3271-3277.
Anand S, Penrhyn-Lowe S, and Venkitaraman AR. Aurora-A amplification overrides the mitotic spindle assembly checkpoint, inducing resistance to Taxol. *Cancer Cell* 2003; 3:51-62.
Andrews PD, Knatko E, Moore WJ, and Swedlow Jr. Mitotic mechanics: the auroras come into view. *Curr Opin Cell Biol* 2003; 15:672-83.
Bischoff Jr, et al., A homologue of *Drosophila aurora* kinase is oncogenic and amplified in human colorectal cancers. *EMBO J* 1998; 17:3052-65.
Carmena M, and Earnshaw WC. The cellular geography of aurora kinases. *Nat Rev Mol Cell Biol* 2003; 4:842-54, 2003.
Castro A, Mandart E, Lorca T, and Galas S. Involvement of Aurora A Kinase during Meiosis I-II Transition in Xenopus Oocytes. *J Biol Chem* 2003; 278:2236-41.
Cheng JQ, Lindsley CW, Cheng GZ, Yang H, and Nicosia SV. The Akt/PKB pathway: molecular target for cancer drug discovery. *Oncogene* 2005; 245:7482-92.
Dan HC, et al., Phosphatidylinositol 3-kinase/Akt Pathway Regulates Tuberous Sclerosis Tumor Suppressor Complex by Phosphorylation of Tuberin. *J Biol Chem* 2002; 277:35364-70.
Dan HC, Sun M, Kaneko S, Feldman RI, Nicosia SV, Wang HG, Tsang BK, and Cheng JQ. Akt Phosphorylation and Stabilization of X-linked Inhibitor of Apoptosis Protein (XIAP). *J Biol Chem* 2004; 279:5405-12.
Fraser M, Leung BM, Yan X, Dan HC., Cheng JQ, and Tsang BK. p53 is a determinant of X-linked inhibitor of apoptosis protein/Akt-mediated chemoresistance in human ovarian cancer cells. *Cancer Res* 2003; 63:7081-8.

(Continued)

*Primary Examiner* — Anna Pagonakis
(74) *Attorney, Agent, or Firm* — Michele L. Lawson; Smith & Hopen, P.A.

(57) ABSTRACT

Most human tumors find ways to resist anticancer drug monotherapy. Akt is considered a likely peptide providing such monotherapy drug resistance. Data indicates that Akt chemoresistance is induced in a p53-dependent manner and that inhibition of Akt may be an effective means of overcoming chemoresistance in cancer cells expressing wild-type p53. Breast, ovarian, lung cancer and leukemia cells lines were treated with combinations of Akt activation inhibitor Triciribine (TCN) or Triciribine phosphate (TCNP) and chemotherapeutic drugs to determine the efficiency of combination therapy. Additionally, cells were introduced into xenograft models to determine in vivo effects of combination treatment. Combining TCN or TCNP with other anticancer drugs overcame cytotoxic or treatment resistance. Thus, TCN and TCNP are shown to broaden the spectrum of human tumors that can be effectively treated.

5 Claims, 51 Drawing Sheets

(56) References Cited

OTHER PUBLICATIONS

Gardai SJ, Hildeman DA, Frankel SK, Whitlock BB, Frasch SC, Borregaard N, Marrack P, Bratton DL, and Henson PM Phosphorylation of Bax Ser184 by Akt regulates its activity and apoptosis in neutrophils. *J Biol Chem* 2004; 279:21085-95.

Giet R, McLean D, Descamps S, Lee MJ, Raff JW, Prigent C, and Glover DM. Drosophila Aurora a Kinase is required to localize D-TACC to centrosomes and to regulate astral microtubules. *J Cell Biol* 2002; 156:437-51.

Goepfert TM, Adigun YE, Zhong L, Gay J, Medina D, and Brinkley WR. Centrosome amplification and overexpression of aurora A are early events in rat mammary carcinogenesis. *Cancer Res* 2002; 62:4115-22.

Gritsko TM, Coppola D, Paciga JE, Yang L, Sun M, Shelley SA, Fiorica JV, Nicosia SV, and Cheng JQ. Activation and Overexpression of Centrosome Kinase Aurora-A in Human Ovarian Cancer. *Clin Cancer Res* 2003; 9:1420-6.

Hsu JY, Sun ZW, et al. Mitotic phosphorylation of histone H3 is governed by IpI1/aurora kinase and Glc7/PP1 phosphatase in budding yeast and nematodes. *Cell* 2000; 102:279-91.

Huang YS, Jung MY, Sarkissian M, and Richter JD. N-methyl-D-aspartate receptor signaling results in Aurora kinase-catalyzed CPED phosphorylation and alpha CaMKII mRNA polyadenylation at synapses. *EMBO J* 2002; 21:2139-48.

Jiang K, Coppola D, Crespo NC, Nicosia SV, Hamilton AD, Sebti SM, and Cheng JQ. The phosphoinositide 3-OH kinase/AKT2 pathway as a critical target for farnesyltransferase inhibitor-induced apoptosis. *Mol Cell Biol* 2000; 20:139-48.

Katayama H, Sasai K, et al. Phosphorylation by aurora kinase a induces Mdm2-mediated destabilization and inhibition of p53. *Nat Genet* 2004; 36:55-62.

Kufer TA, Sillje HH, Korner R, Gruss OJ, Meraldi P, and Nigg EA. Human TPX2 is required for targeting Aurora-A kinase to the spindle. *J Cell Biol* 2002; 158:617-23.

Li D, Zhu J, Firozi PF, Abbruzzese JL, Evans DB, Cleary K, Friess H, and Sen S. Overexpression of oncogenic STK15/BTAK/Aurora A kinase in human pancreatic cancer. *Clin. Cancer Res* 2003; 9:991-7.

Liu Q, Kaneko S, Yang L, Feldman RI, Nicosia SV, Chen J, and Cheng JQ. Aurora-A abrogation of p53 DNA binding and transactivation activity by phosphorylation of serine 215. J Biol Chem 2004; 279:52175-82.

Mandic A, Viktorsson K, et al. Calpain-mediated Bid cleavage and calpain-independent Bak modulation: two separate pathways in cisplatin-induced apoptosis. *Mol Cell Biol* 2002; 22:3003-13.

Mills AA. p53: link to the past, bridge to the future. Genes Dev 2005; 19:2091-9.

Moreno-Bueno G, Sanchez-Estevez C, et al. Differential gene expression profile in endometrioid and nonendometrioid endometrial carcinoma: STK15 is frequently overexpressed and amplified in nonendometrioid carcinomas. *Cancer Res* 2003; 63:5697-702.

Park MS, De Leon M, and Devarajan P. Cisplatin induces apoptosis in LLC-PK1 cells via activation of mitochondrial pathways. *J Am Soc Nephrol* 2002; 13:858-65.

Sakakura C, Hagiwara A, et al. Tumour-amplified kinase BTAK is amplified and overexpressed in gastric cancers with possible involvement in aneuploid formation. *Br J Cancer* 2001; 84:824-31.

Sasaki H, Sheng YL, Kotsuji F, and Tsang BK. Down-regulation of X-linked inhibitor of apoptosis protein induces apoptosis in chemoresistant human ovarian cancer cells. *Cancer Res* 2000; 60:5659-66.

Scrittori L, Hans F, Angelov D, Charra M, Prigent C, and Dimitrov S. pEg2 aurora-A kinase, histone H3 phosphorylation, and chromosome assembly in Xenopus egg extract. *J Biol Chem* 2001; 276:30002-10.

Sen S, Zhou H, and White RA. A putative serine/threonine kinase encoding gene BTAK on chromosome 20q13 is amplified and overexpressed in human breast cancer cell lines. *Oncogene* 1997; 14:219-200.

Sen S, Zhou H, Zhang RD, et al. Amplification/overexpression of a mitotic kinase gene in human bladder cancer. *J Natl Cancer Inst* 2002; 94:1320-9.

Singh B, Reddy PG, et al. p53 regulates cell survival by inhibiting PIK3CA in squamous cell carcinomas. *Genes Dev* 2002; 16:984-93.

Stambolic V, MacPherson D, Sas D, Lin Y, Snow B, Jang Y, Benchimol S, and Mak TW. Regulation of PTEN transcription by p53. *Mol. Cell* 2001; 8:317-25.

Tanner MM, Grenman S, Koul A, Johannsson O, Meltzer P, Pejovic T, Borg A, and Isola JJ. Frequent amplification of chromosomal region 20g12-q13 in ovarian cancer. *Clin. Cancer Res* 2000; 6:1833-9.

Yang H, Ou CC, Feldman RI, Kruk PA, Nicosia SV, and Cheng JQ. Aurora-A Upregulates Human Telomerase Reverse Transcriptase through Activation of c-Myc Transcription. *Cancer Res* 2004; 64:463-7.

Yang L, Dan HC, et al.. Akt/Protein kinase B signaling inhibitor-2, a selective small molecule inhibitor of Akt signaling with antitumor activity in cancer cells overexpressing Akt . . . *Cancer Res* 2004; 64:4394-9.

Yuan ZQ, Sun M, Feldman RI, Wang G, Ma X, Coppola D, Nicosia SV. and Cheng JQ. Frequent activation of AKT2 and induction of apoptosis by inhibition of phosphoinositide-3-OH kinase/Akt pathway in human ovarian cancer. *Oncogene* 2000; 19:2324-30.

Zhou H, Kuang J, Zhong L, Kuo, WL, Gray JW, Sahin A, Brinkley BR, and Sen S. Tumour amplified kinase STK15/BTAK induces centrosome amplification, aneuploidy and transformation. *Nat Genet* 1998; 20:189-93.

Tallarida, R. J. 2001. "Drug Synergism: Its Detection and Applications." The Journal of Pharmacology and Experimental Therapeutics. vol. 298. No. 3. pp. 865-872.

Voigt et al. 2000. "Schedule-Dependent Antagonism of Gemcitabine and Cisplatin in Human Anaplastic Thyroid Cancer Cell Lines." Clinical Cancer Research. vol. 6. pp. 2087-2093.

Chou et al. 1994. "Computerized Quantitation of Synergism and Antagonism of Taxol, Topotecan, and Cisplatin Against Human Teratocarcinoma Cell Growth: a Rational Approach to Clinical Protocol Design." Journal of National Cancer Institute. vol. 86. No. 20. pp. 1517-1524.

Riedel et al. 2008. "A Genomic Approach to ldentfy Molecular Pathways Associated with Chemotherapy Resistance." Mol. Cancer Ther. vol. 7. No. 10. pp. 3141-3149.

Chou. 2006. "Theoretical Basis, Experimental Design, and Computerized Simulation of Synergism and Antagonism in Drug Combination Studies." Pharmacological Reviews. vol. 58. pp. 621-681.

Tallarida. 2006. "An Overview of Drug Combination Analysis with lsobolograms." The Journal of Pharmacology and Experimental Therapeutics. vol. 319. No. 1. pp. 1-7.

Tallarida. 2001. "Drug Synergism: Its Detection and Applications." The Journal of Pharmacology and Experimental Therapeutics. vol. 298. No. 3. pp. 865-872.

Fedier, A.; Erdmann, R.; Boulikas, T.; Fink, D. Potential of the Akt inhibitor LY294005 to antagonize the efficacy of Cisplatin against HCT116 tumor cells in DNA mismatch repair-dependent manner. International Journal of Oncology, 29: 1303-1310, 2006.

Shingu, T.; Yamada, K.; Hara, N.; Moritake, K.; Osago, H.; Terashima, M.; Uemura, T.; Yamasaki, T.; Tsuchiya, M. Synergistic Augmentation of Antimicrotubule Agent-induced Cytotoxicity by a Phosphoinositide 3-Kinase Inhibitor in Human Malignant Glioma Cells. Cancer Research, 63:4044-4047, Jul. 15, 2003.

Fedier, A.; Erdmann, R. A.; Dedes, K. J.; Imesch, P.; Boulikas, T.; Fink, D. Modulation of platinum drug sensitivity by the Akt inhibitor LY294005 in MMR-proficient and MMR-deficient HCT116 colon tumor cells. Proc Mer Assoc Cancer Res, vol. 47, 2006.

Kelland, The resurgence of platinum-based cancer chemotherapy, Nature Reviews, Cancer, 2007, vol. 7, pp. 573-584.

\* cited by examiner

Rapamycin and RAD001 inhibition of cell growth is enhanced by TCN
A
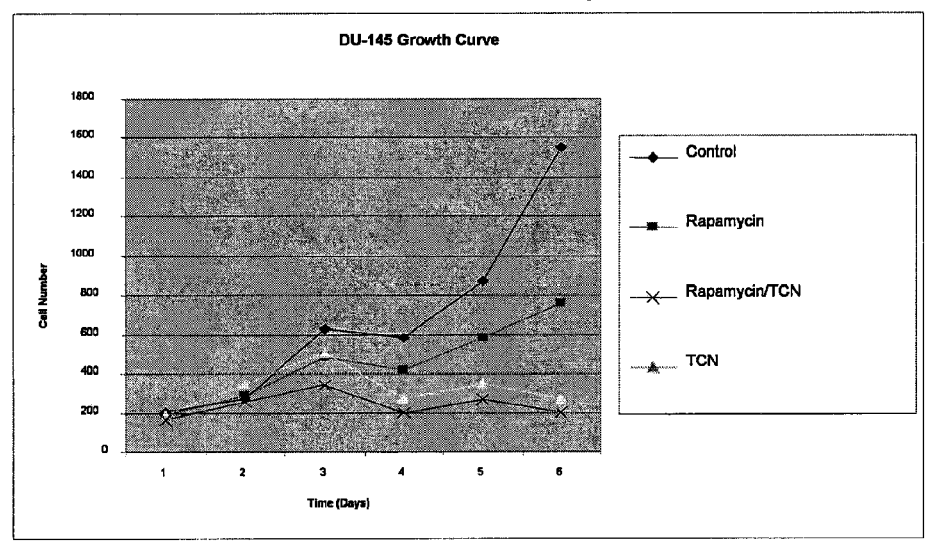
B
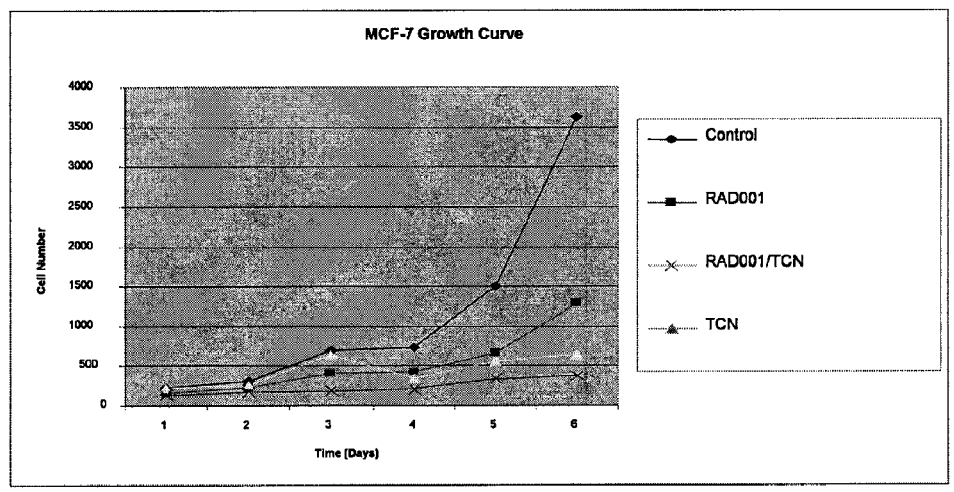
Figure 13.

Rapamycin and RAD001 inhibition of cell growth is enhanced by TCN

TCN overcomes CDDP resistance

Synergistic effect of TCN and CDDP on cell survival in C-13 cell line

TCN/API-2 overcomes Aurora-A induced CDDP resistance
A
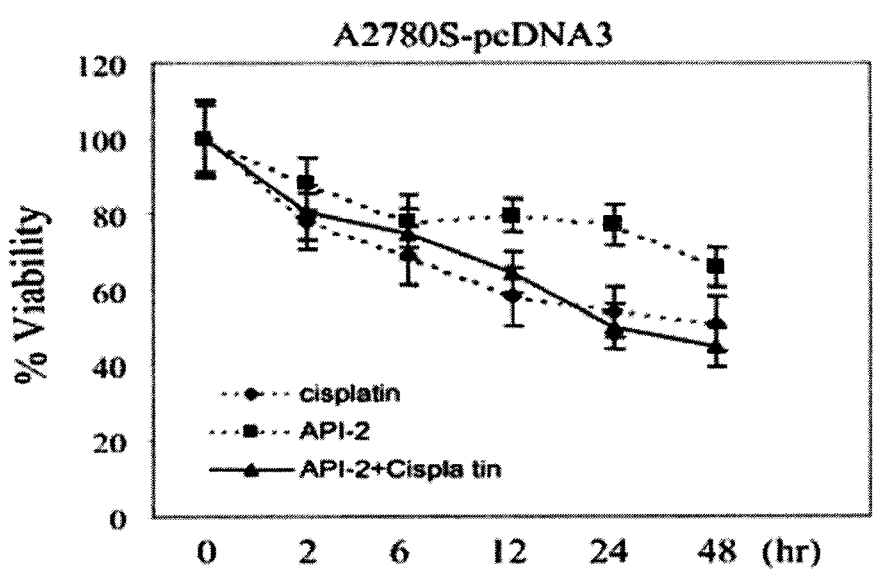
B
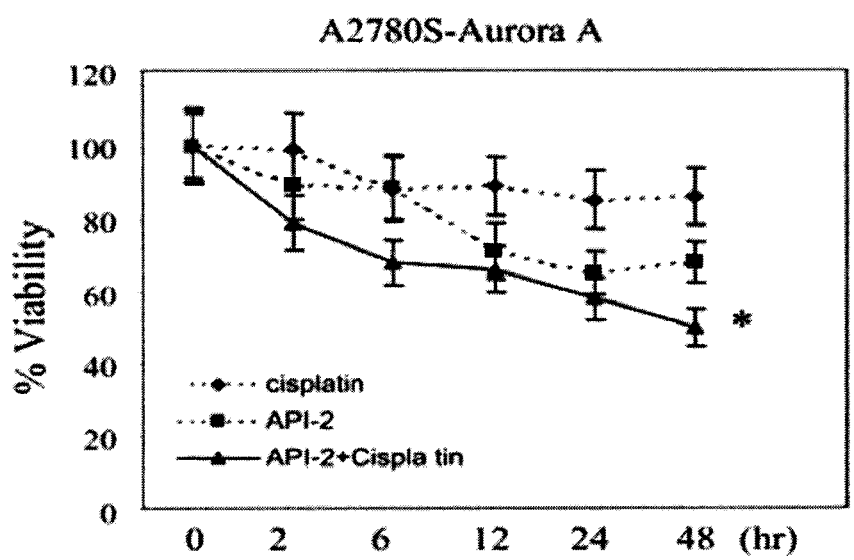
Figure 17.

TCN/API-2 overcomes Aurora-A induced CDDP resistance

Synergistic effect of TCN and Taxol on apoptosis in A2780S and OVCAR3 cells

TCN enhances the ability of CDDP to inhibit the growth C13 cells in nude mouse xenografts

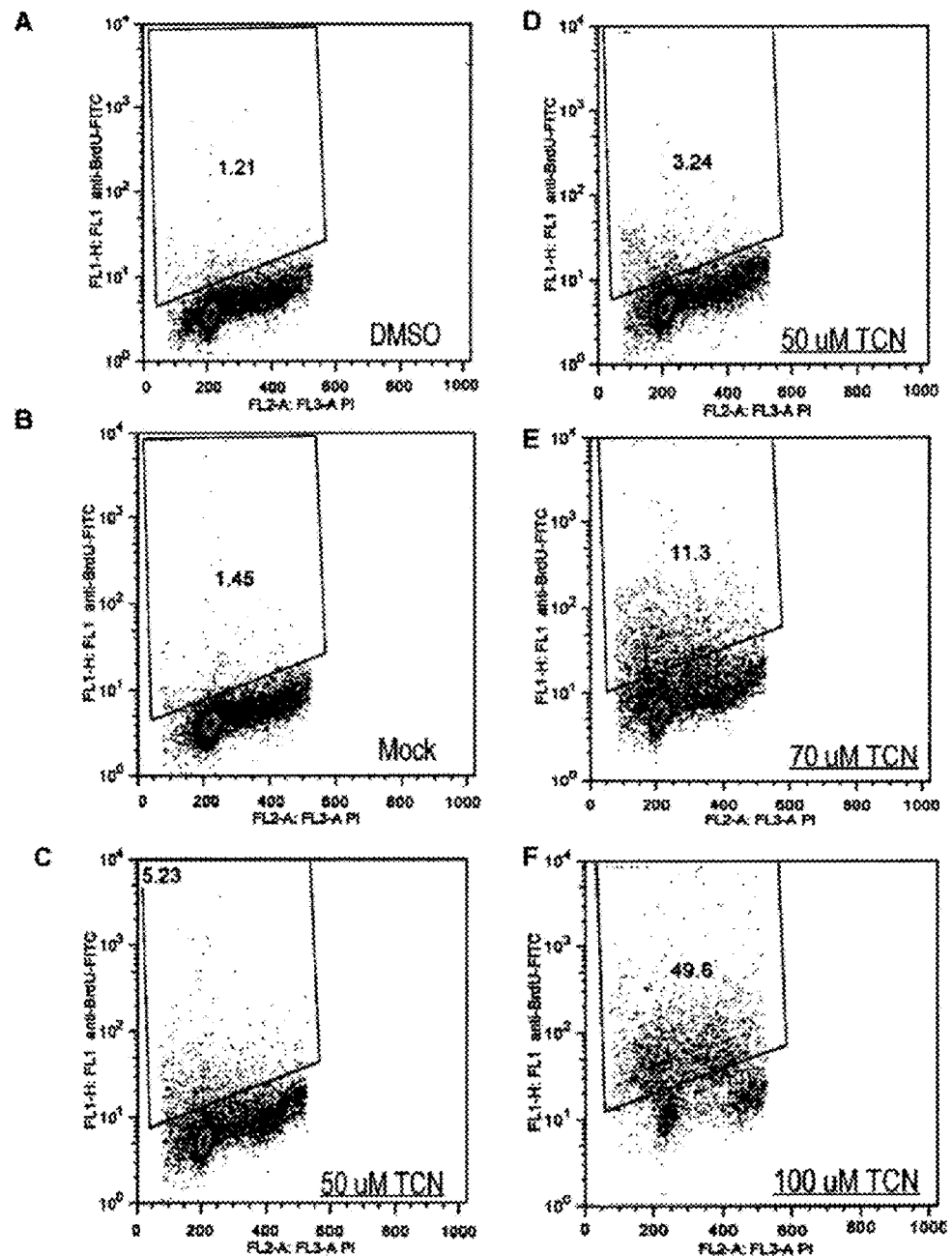
Figure 25A-F

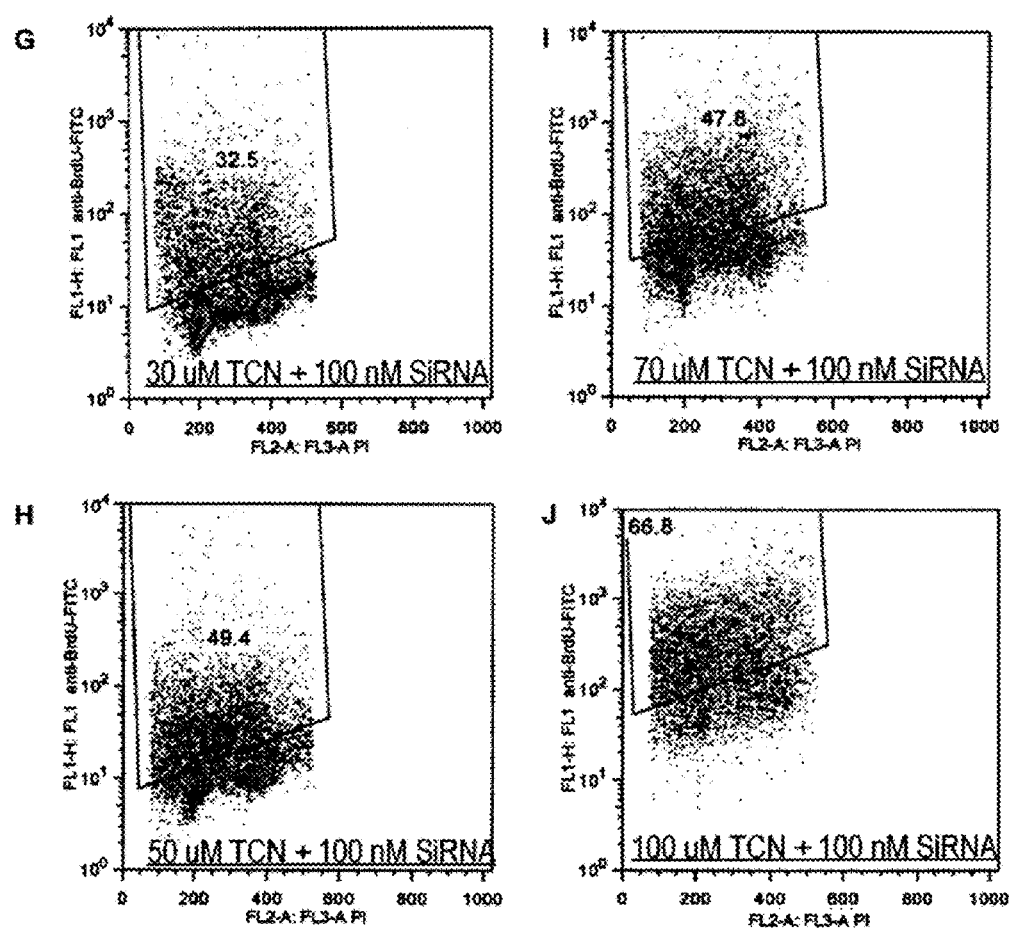
Figure 25G-J

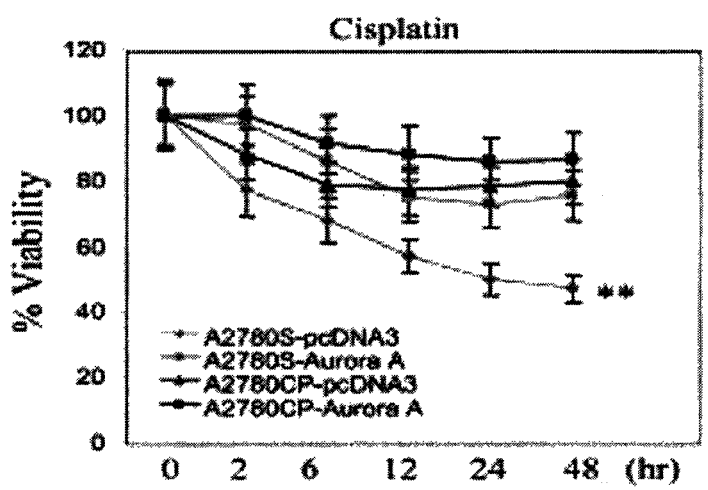
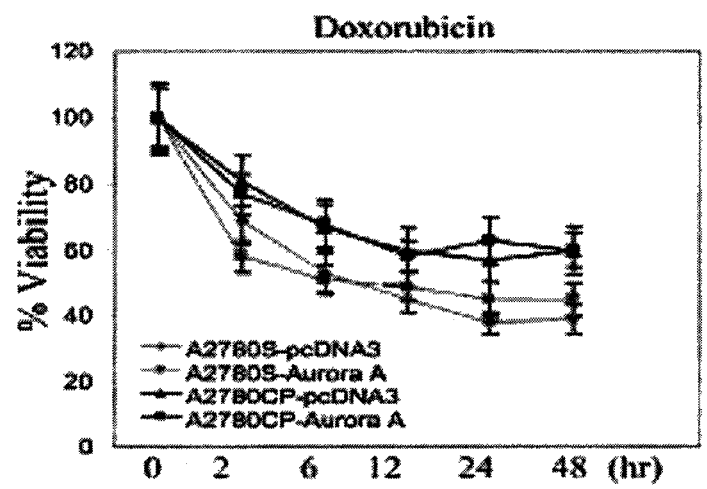
Figure 29.

A 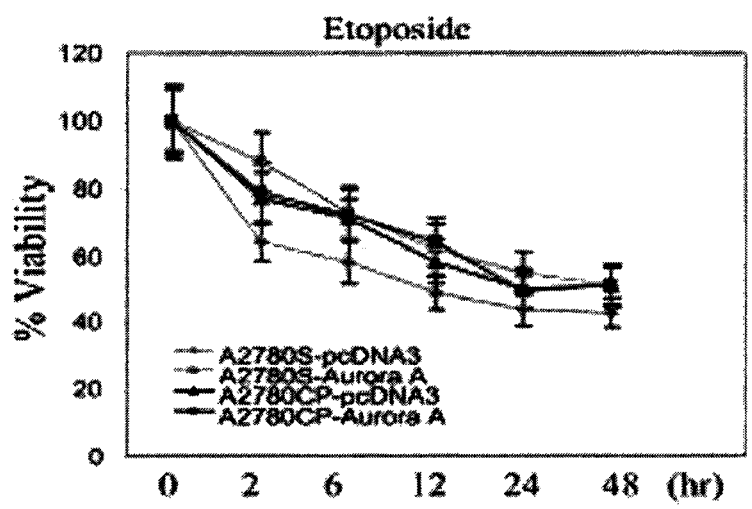
B 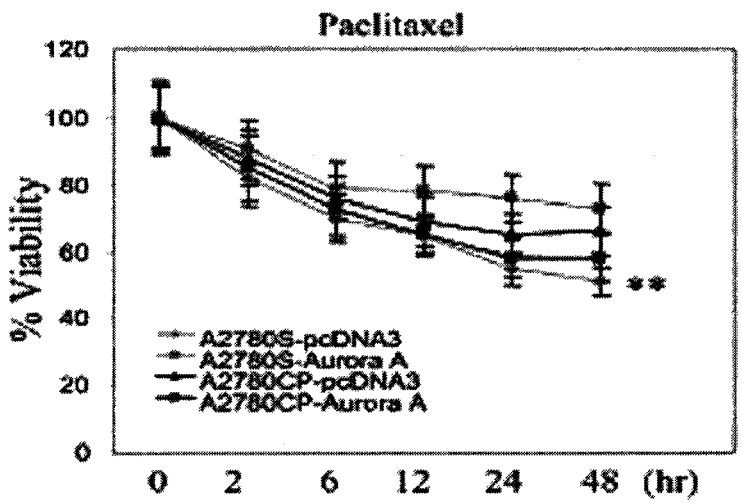
Figure 30.

A 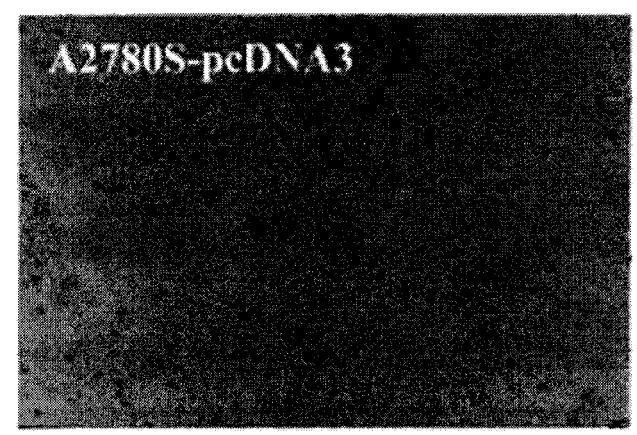
B 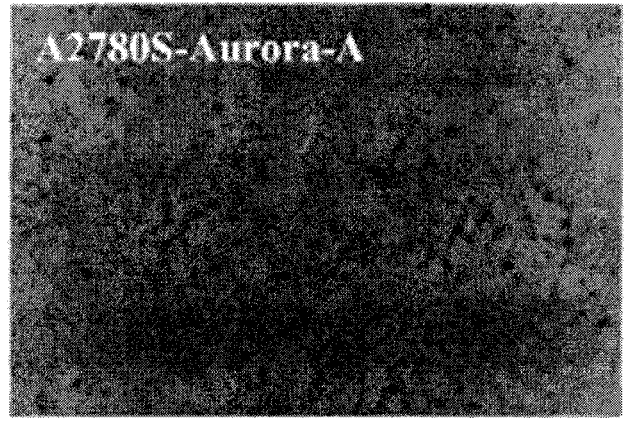
Figure 33.

Treatment of the human lung cancer cell line A-549 with the Akt activation inhibitor TCN and the farnesyltransferase inhibitor FTI-2153 results in a synergistic inhibition of tumor cell growth Treatment of the human lung cancer cell line A-549 with the Akt activation inhibitor TCN and the farnesyltransferase inhibitor FTI-2153 results in a synergistic inhibition of tumor cell growth Treatment of the human lung cancer cell line A-549 with TCN and the farnesyltransferase inhibitor Tipifarnib results in a synergistic inhibition of tumor cell growth TCN blocked the ability of Tipifarnib to increase P-Akt levels in A-549 cancer cells Treatment of the human breast cancer cell line MA-MB-231 with TCN and Tipifarnib results in a synergistic inhibition of tumor cell growth Treatment of the human breast cancer cell line MA-MB-231 with TCN and Tipifarnib results in a synergistic inhibition of tumor cell growth Treatment of the human breast cancer cell line MCF-7 with TCN and Tipifarnib results in a synergistic inhibition of tumor cell growth Treatment of the human breast cancer cell line MCF-7 with TCN and Tipifarnib results in a synergistic inhibition of tumor cell growth Treatment of the human multiple myeloma cell line U266 with TCN and Tipifarnib results in a synergistic inhibition of tumor cell death Treatment of the human leukemia cell line MV4-11 with TCN and Tipifarnib results in a synergistic induction of tumor cell death Treatment of the human leukemia cell line MV4-11 with TCN and Tipifarnib resulted in a synergistic inhibition of tumor cell growth Treatment of the human leukemia cell line MV4-11 with TCN and Tipifarnib resulted in a synergistic inhibition of tumor cell growth
A
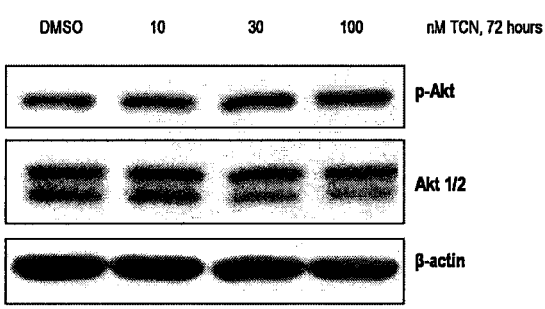
B
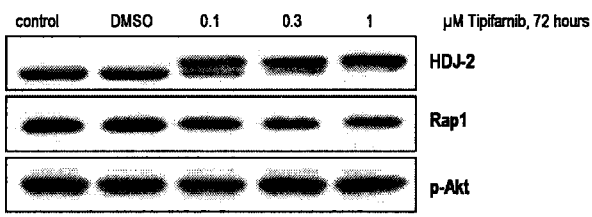
Figure 55.

Treatment of the human leukemia cell line HL60 with TCN and Tipifarnib resulted in a synergistic induction of tumor cell death
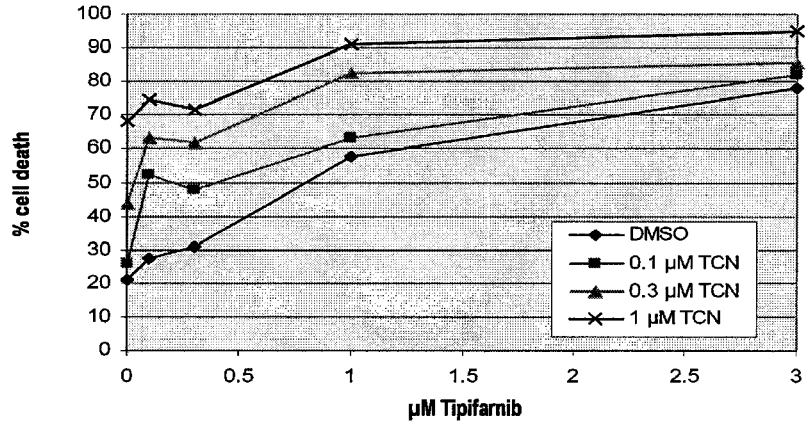
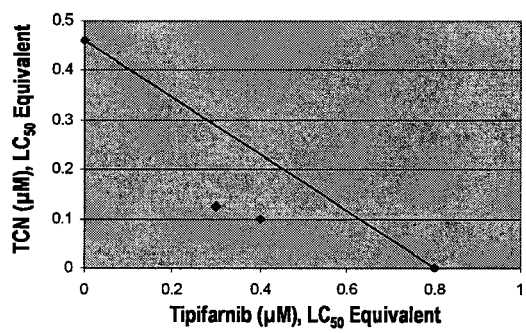
Figure 56.

Treatment of the human leukemia cell line HL60 with TCN and Tipifarnib resulted in a synergistic inhibition of tumor cell growth Treatment of the human leukemia cell line HL60 with TCN and Tipifarnib resulted in a synergistic inhibition of tumor cell growth

AKT SENSITIZATION OF CANCER CELLS

CROSS REFERENCE TO RELATED APPLICATION

This application claims priority to U.S. Provisional Patent Application No. 60/828,154, entitled "Combination of the Akt Activation Inhibitor Triciribine/Triciribine Phosphate with Cytotoxic and Anti-Signaling Molecules for Cancer Therapy", filed on Oct. 4, 2006, the contents of which are herein incorporated by reference.

GOVERNMENT SUPPORT

This invention was made with government support under CA67771, CA098473, CA106829, CA107078, CA077935, and CA089242 awarded by the National Institutes of Health. The government has certain rights in the invention

FIELD OF INVENTION

This invention relates to cancer treatment using a combination treatment approach. Specifically, the Akt pathway is targeted to sensitize cancerous cells to one or more other cancer treatment drugs.

BACKGROUND OF THE INVENTION

Most human tumors find ways to resist anticancer drug monotherapy. Akt is considered a likely peptide providing such monotherapy drug resistance. Aurora-A, a serine/threonine protein kinase, activates the Akt pathway in a p53-dependent manner, and thus protects cancer cells from chemotherapeutic-induced apoptosis often involved in cancer resistance to anticancer drug monotherapy.

Akt, also called protein kinase B, is a serine/threonine protein kinase that is activated by extracellular stimuli in a phosphatidylinositol 3'-kinase (PI3k)-dependent manner. Akt has emerged as a crucial regulator of a wide range of cellular processes including apoptosis, proliferation, differentiation, and metabolism. Akt is phosphorylated, and therefore activated, by phosphoinositide dependent kinase 1 (PDK1) and the mammalian target of rapamycin complex 2 (mTORC2). Deregulation of the Akt signaling pathway has been documented as a frequent occurrence in a number of human malignancies. Ectopic expression of Akt induces cell survival and malignant transformation, whereas inhibition of Akt activity stimulates apoptosis. Furthermore, over-expression of active Akt often accompanies increased chemoresistance in cancer cells.

Cisplatin [CDDP, cis-Diammine-dicholoroplatinum(II)], an anti-tumor drug known to induce apoptosis of cancer cells by damaging nuclear DNA, is among the most effective agents used in human cancer chemotherapy. CDDP increases p53 content, leading to up-regulation of proteins promoting cell cycle arrest, such as p21, and of pro-apoptotic proteins such as Bax and Fas leading to activations of both the mitochondrial and death-receptor apoptotic pathways, resulting in the activation of the execution caspase-3 and -7.

Taxol is a plant alkaloid anti-tumor drug which acts on microtubule growth during mitosis. Taxol stabilizes the β tubulin subunit of the microtubule, preventing the dissociation of the microtubule preventing cellular transport and further mitosis. Taxol has likewise been shown to induce apoptosis by stopping Bcl-2.

Farnesyltransferase inhibitors (FTI) and geranylgeranyltransferase inhibitors (GGTI) target farnesyltransferase and geranylgeranyltrasferase, respectively, preventing posttranscriptional modification and function of the Ras protein. Conversely, proteasome inhibitors prevent proteasome activity, preventing the degradation of proteins. Recent proteasome inhibitors selectively abrogate proteasome activity by reacting with the hydroxyl group and N-terminal theronine in the proteasome's active site.

Chemoresistance represents a major obstacle for successful cancer therapy. Increased dosage is required for resistant cells; however large dose treatments often lead to severe side effects in multiple organs.

Akt over expression often accompanies increased chemoresistance in cancer cells. Several studies have established mechanisms by which Akt may contribute to CDDP resistance. For instance, Akt attenuates the CDDP-mediated up-regulation of p53. Phosphorylation of MDM2 by Akt inactivates p53 and in turn prevents p53-mediated cell cycle arrest. Akt also protects anti-apoptotic proteins such as XIAP from CDDP-induced down-regulation. In addition, Akt activity promotes cellular resistance to CDDP through the inhibitions of CDDP-induced JNK and p38 activations required for CDDP's anti-tumor activity

SUMMARY OF INVENTION

The invention provides a method of treating cancer, through a combination drug treatment. Akt expression renders cells resistant to cisplatin (CDDP), etoposide and paclitaxel-induced apoptosis. Akt1 and Akt2 may be stimulated by Aurora-A activity, providing chemotherapy resistance within wild-type p53 but not p53-null cancer cells. Knockdown of Aurora-A by RNAi sensitizes cells to CDDP-induced apoptosis and decreases phospho-Akt levels in wild-type p53 cells. Reintroduction of p53 decreases Akt1 and Akt2 activation and restores CDDP. Introduction of TCN (also referred to herein as "API-2"), overcomes the effects of Aurora-A on cell survival and Bax mitochondrial translocation by inhibiting Akt. Taken collectively, these data indicate that Akt chemoresistance is induced in a p53-dependent manner and that inhibition of Akt may be an effective means of overcoming chemoresistance in cancer cells expressing wild-type p53.

Therefore, this invention provides that inhibiting Akt activation will lead to sensitization of tumors to anticancer drugs including cytotoxic agents such as cisplatins and taxanes and anti-signaling agents such as farnesyltransferase inhibitors (FTIs); geranylgeranyltransferase inhibitors (GGTIs); mammalian target of rapamycin (mTOR) inhibitors such as rapamycin and RAD 001; Mek inhibitors such as U0126, STAT3 inhibitors such as JSI-124 and Withacnistin, receptor tyrosine kinase inhibitors such as the EGFR inhibitors IRESSA and Tarceva, proteasome inhibitors such as HL-1 and Velcade, ErbB2 antibodies such as Herceptin, EGFR inhibitors such as Erbitux, VEGF antibodies such as Avastin, VEGF/PDGF binding molecules such as GFB-204, Raf inhibitors such as Bay compound. Combining the Akt activation inhibitor Triciribine or Triciribine phosphate with other anticancer drugs will overcome this resistance and broaden the spectrum of human tumors that can be effectively treated.

In one embodiment, Triciribine or Triciribine Phosphate is coadministered with a cytotoxic, anti-signaling or other anti-cancer agent to treat a cancerous cell or mass. The invention decreases the likelihood of tumor survival, as cancerous cells cannot activate Akt to overcome anticancer drugs. The method involves a synergistic action between an Akt inhibitor and an anticancer drug, removing a survival pathway and inhibiting the growth potential of the cancerous cells.

In another embodiment, the invention provides for increasing the response of Akt-activated tumors to anticancer drugs. Akt-activated tumors are more difficult to treat, due to the enhanced survivability of the tumor against the anticancer drug provided by Akt pathways. Disrupting Akt during traditional anticancer treatment removes the Akt survival pathway, allowing the traditional drugs to effectively eliminate cancer cells via apoptosis.

BRIEF DESCRIPTION OF THE DRAWINGS

For a fuller understanding of the invention, reference should be made to the following detailed description, taken in connection with the accompanying drawings, in which:

FIG. 13 depicts the inhibition of cell growth after combination treatment of mTOR inhibitor with API-2 (TCN). (A) DU-145 human prostate cancer and (B) MCF-7 human breast cancer cell lines were treated with 1 nM rapamycin (DU-145 cells only), 25 nM RAD001 (MCF-7 cells only), 5 μM API-2, or a combination of API-2 with rapamycin or RAD001. Cell numbers were measured for six days after treatment. Rapamycin and RAD001 inhibited cell growth, while TCN provided a similar inhibitory effect of cell numbers. However, cell growth was further inhibited by combination treatment.

FIG. 17 shows cell survival for CDDP-resistant cells after treatment. CDDP-resistant A2780CP cells (A) without (B) or with Aurora-A were grown in 96 well plates and treated with 10 μM CDDP, 10 μM API-2, or a combination of CDDP and API-2. 24 hr following treatment, the cells were assayed using Capase-Glo™ 3/7.

SiRNA 152, TCN or a combination of the agents for 72 hr. The effects of Stat3 SiRNA, alone and in combination with TCN, on target proteins was analyzed.

Figure 24:
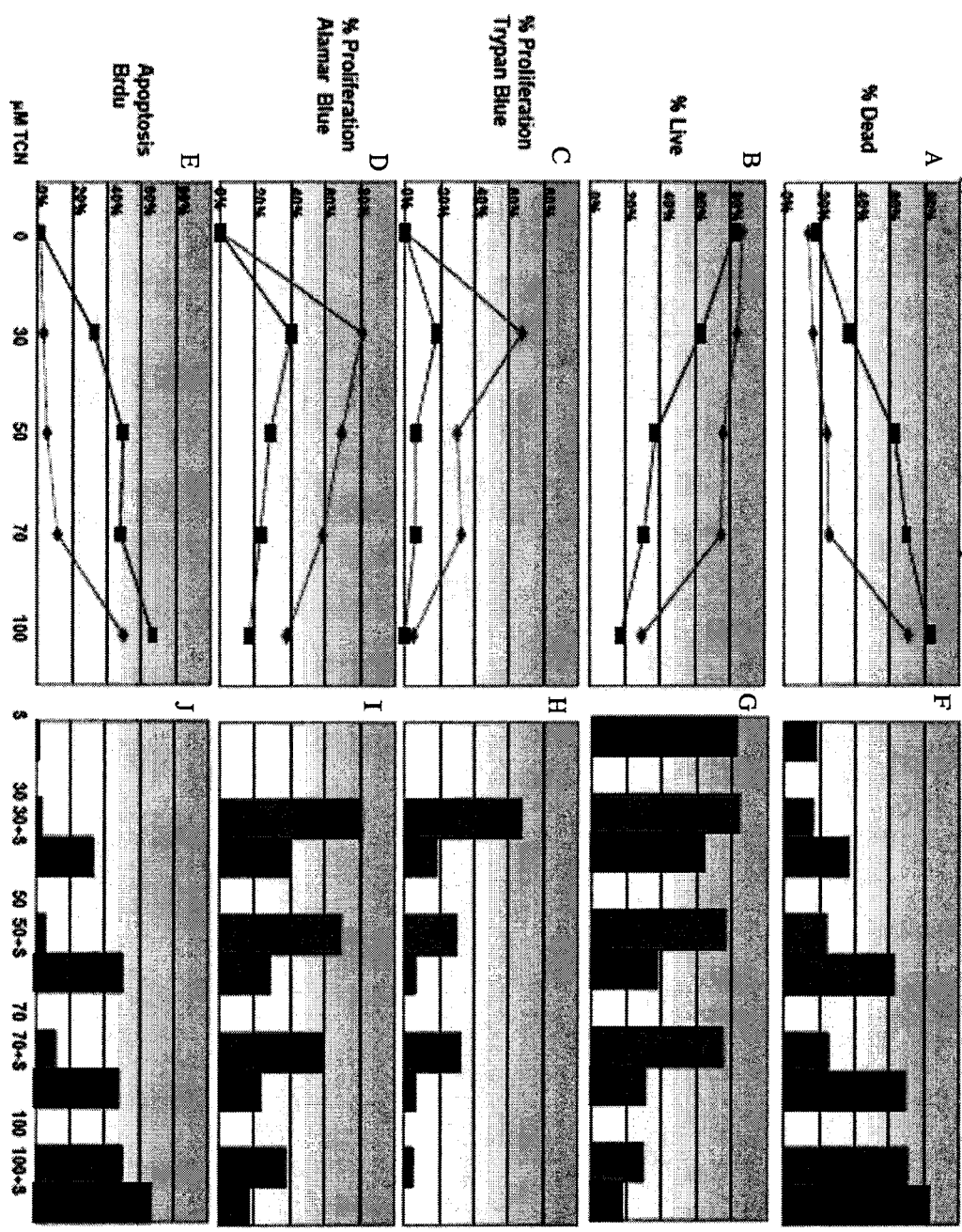

FIG. 24 shows (A, B) survivability, (C, D) proliferation, and (E) apoptosis graphs and (F, G) survivability, (H, I) proliferation, and (J) apoptosis bar charts of cancer cells after treatment. MDA-MB-435 breast cancer cells were treated with TCN and STAT3 siRNA. Cell survival, proliferation, and programmed cell death were analyzed at 24 hr for indicated levels of TCN. TCN enhanced the ability of STAT3 siRNA to inhibit proliferation and induce tumor cell death.

FIG. 25 shows cell cycle status of cancer cells after combination treatment. Human breast cancer cell line MDA-MB-435 was treated with siRNA against STAT 3. The transfected cells were then administered (A) DMSO, (B) nothing, (C, D) 50 μM TCN, (E) 70 μM TCN, (F) 100 μM TCN, (G) 30 μM TCN with 100 nM siRNA, (H) 50 μM TCN with 100 nM siRNA, (I) 70 μM TCN with 100 nM siRNA, and (J) 100 μM TCN with 100 nM siRNA. Cells were stained and FACS analysis performed after 24 hr to determine cell cycle status. The combination treatment enhances the ability of STAT3 siRNa to induce apoptosis.

Figure 26:
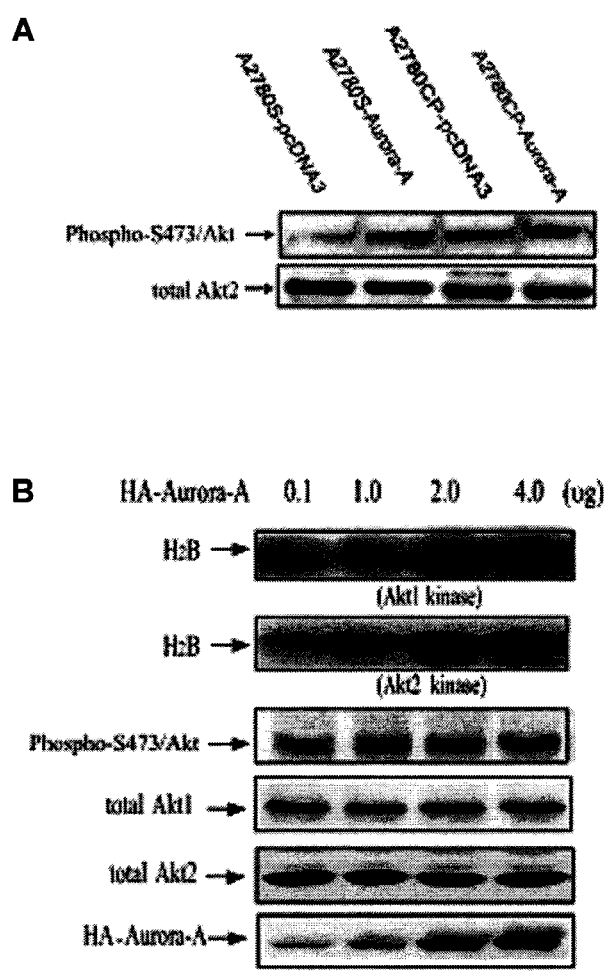

FIG. 26 shows Aurora-A activates Akt. Wild type p53 A2780S and mutant p53 A2780CP cells were transfected with Aurora-A. (A) Western blot for phosphor-Akt-S473 and total Akt levels indicate Aurora-A activates Akt. (B) Cells were transfected with HA Aurora-A and precipitated with Akt1 and Akt2 antibodies. Akt1 and Akt2 kinase activity was measured in vitro using histone H2B as a substrate (top panels). Protein extracts were analyzed with indicated antibodies (bottom panels).

Figure 27:
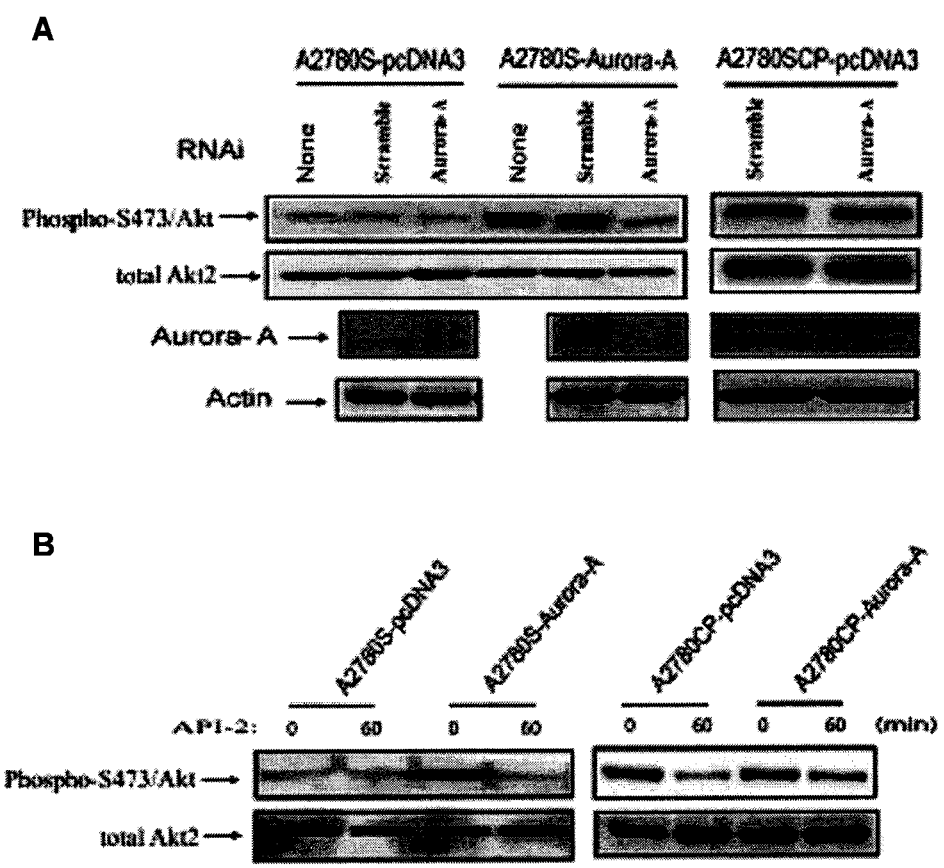

FIG. 27 shows Aurora-A transfected cells transfected cancer cell survival and protein expression. Wild type p53 A2780S and mutant p53 A2780CP cells were transfected with Aurora-A. (A) Cells were treated with Aurora-A siRNA or scramble RNAi for 48 hr, lysed and immunoblotted with indicated antibodies. (B) Cells were treated with API-2. 1 hr later, cells were lysed and immunoblotted with anti-phospho-Akt-S473 (top) and anti-Akt (total) antibodies.

Figure 28:
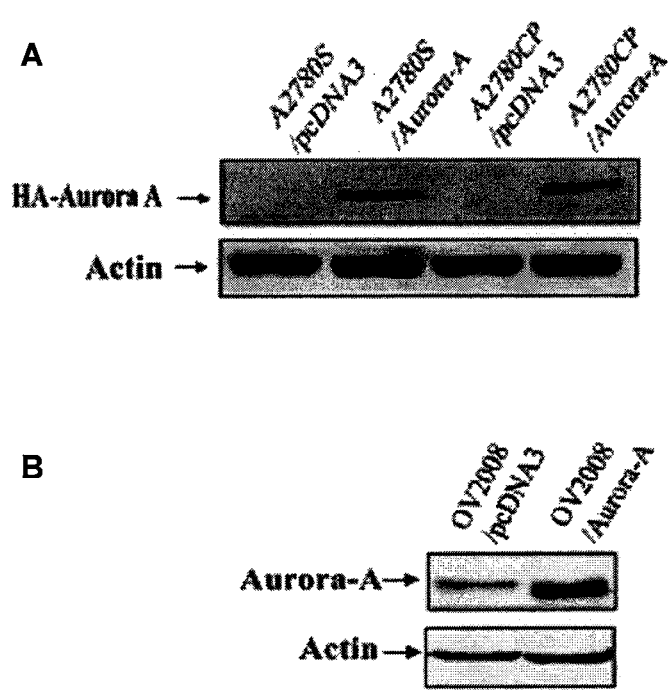

FIG. 28 shows Aurora-A transfected cancer cell survival and protein expression. Wild type p53 A2780S and mutant p53 A2780CP cells were transfected with HA Aurora-A or a control. (A) Cell lysates were immunoblotted with anti-HA (top panel) and anti-actin (bottom panel) antibodies. Aurora A induced chemoresistance in wild-type p53 cells. (B) OV2008 were transfected as indicated and immunoblotted with anti-Aurora-A antibody.

FIG. 29 shows Aurora-A transfected cancer cell survival and protein expression. Wild type p53 A2780S and mutant p53 A2780CP cells were transfected with HA Aurora-A or a control. (A) Cells were treated with 10 μM CDDP or (B) 2 μM doxorubicin for indicated times and analyzed by MTT assay. Results represent an average of three trial runs. Aurora-A induced chemoresistance in A2780S, but not A2780CP, cells.

FIG. 30 shows Aurora-A transfected cancer cell survival and protein expression. Wild type p53 A2780S and mutant p53 A2780CP cells were transfected with HA Aurora-A or a control. (A) Cells were treated with 5 μM VP16 or (B) 100 nM Taxol for indicated times and analyzed by MTT assay. Results represent an average of three trial runs. Aurora-A induced chemoresistance in A2780S, but not A2780CP, cells. **p<0.01.

Figure 31:
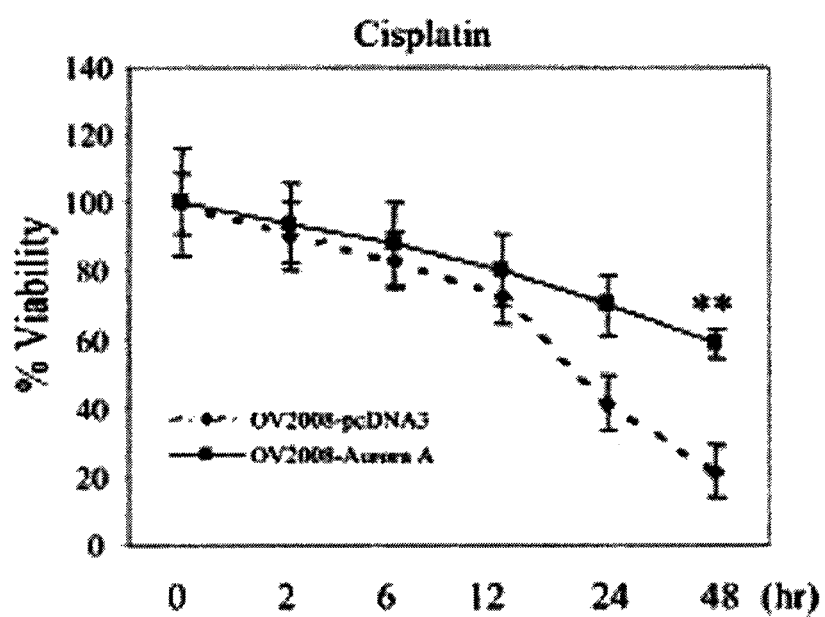

FIG. 31 shows Aurora-A transfected cancer cell survival apoptosis after CDDP treatment. OV2008 were transfected as indicated and immunoblotted with anti-Aurora-A antibody. Transfected cells were treated with 15 μM CDDP for indicated times and cell death was analyzed. Overexpression of Aurora-A rendered OV2008 cells resistant to CDDP. **p<0.01.

Figure 32:
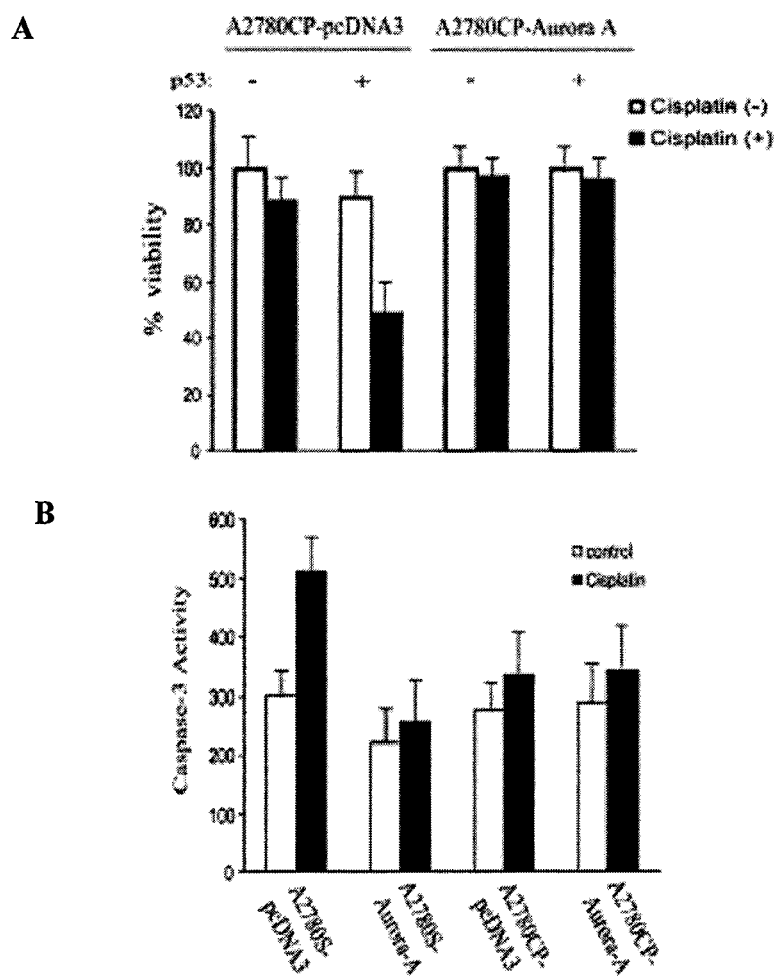

FIG. 32 shows Aurora-A transfected cancer cells survival and apoptosis after CDDP treatment. Wild type p53 A2780S and mutant p53 A2780CP cells were transfected with HA Aurora-A or a control as indicated. (A) Cells were infected with adenovirus WT-p53 or adenovirus alone and treated with CDDP or vehicle for 24 hr. MTT assay was used to determine cell viability. Results represent the average of three runs. Ectopically expressed wild-type p53 restored CDDP sensitivity. (B) After treatment with CDDP, cells were lysed and assayed for caspase-3 activity using EnzChek Caspase-3 Assay kit (Molecular Probes). Aurora-A inhibited CDDP-induced caspase-3 activity.

FIG. 33 shows Aurora-A transfected cancer cells survival apoptosis after CDDP treatment. (A) Wild type p53 A2780S and (B) mutant p53 A2780CP cells were transfected with HA Aurora-A or a control. Cells were treated with 10 μM CDDP for 24 hr and subjected to Tunel assay.

Figure 34:
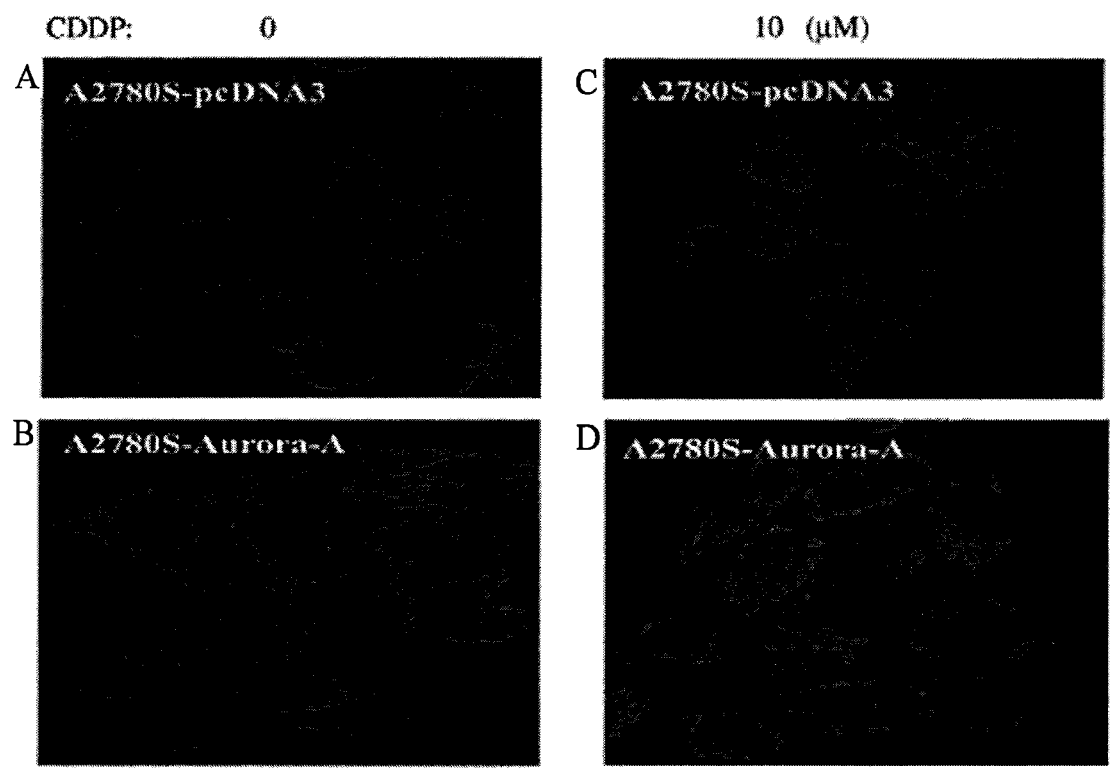

FIG. 34 shows Aurora-A RNAi knockdown reduces tumor survivability after CDDP treatment. Wild type p53 A2780S cells were transfected with (A, C) pcDNA3 control or (B,D) HA Aurora-A. Cells were treated (A, B) without and (C, D) with CDDP for 6 hr and stained with DAPI and anti-cytochrome C antibody. Aurora-A reduced cytochrome C release.

Figure 35:
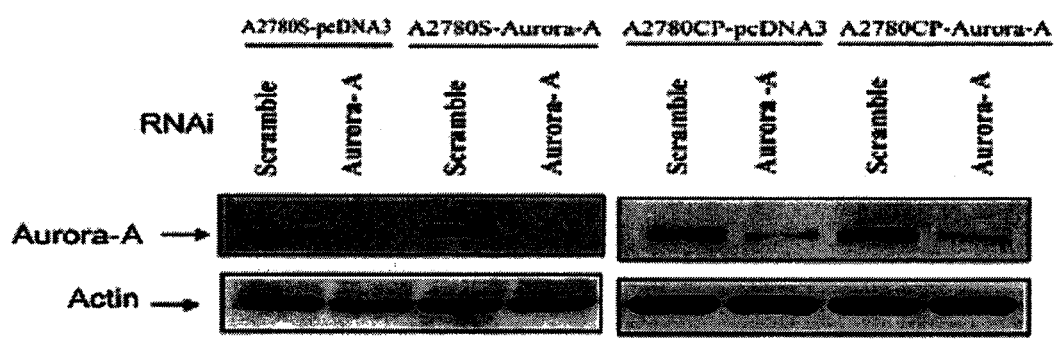

FIG. 35 shows Aurora-A RNAi knockdown reduces tumor cell survivability after CDDP treatment. A2780S and A2780CP cells were transfected as indicated. 48 hr after transfection, cells were lysed and immunoblotted with anti-Aurora-A (upper panel) and anti-actin (bottom panel) antibodies.

Figure 36:
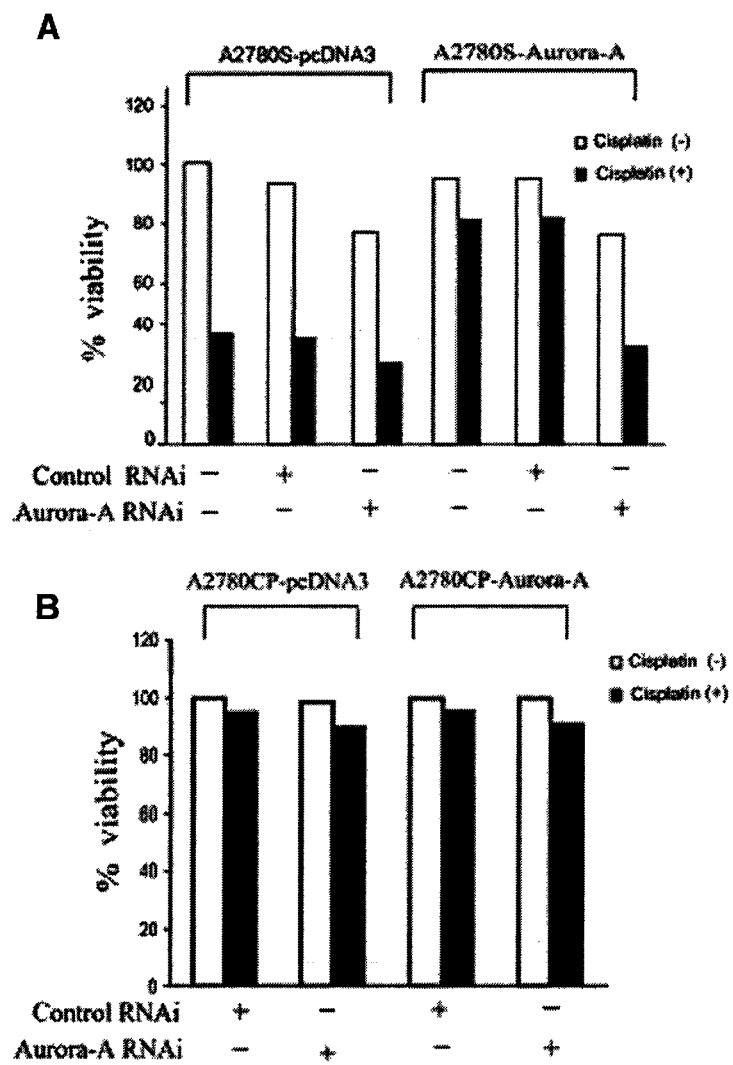

FIG. 36 shows Aurora-A RNAi knockdown reduces tumor cell survivability after CDDP treatment. (A) A2780S and (B) A2780CP cells were transfected as indicated. Cells were treated with RNAi and exposed to CDDP or vehicle for 24 hr. Cell viability and apoptosis were examined by MTT assay.

Figure 37:
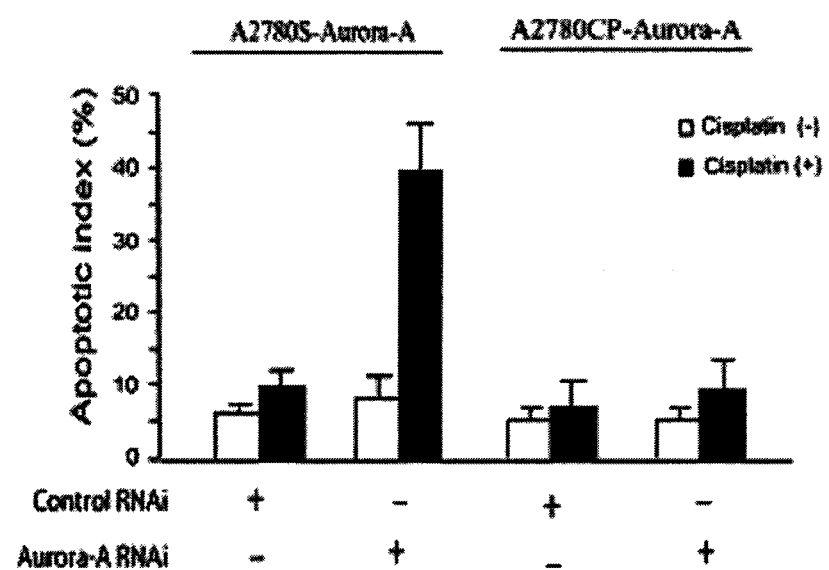

FIG. 37 shows Aurora-A RNAi knockdown reduces tumor cell survivability after CDDP treatment. A2780S and A2780CP cells were transfected as indicated. Cells were treated with RNAi and exposed to CDDP or vehicle for 24 hr. Cell viability and apoptosis were examined by and Tunnel assay.

Figure 38:
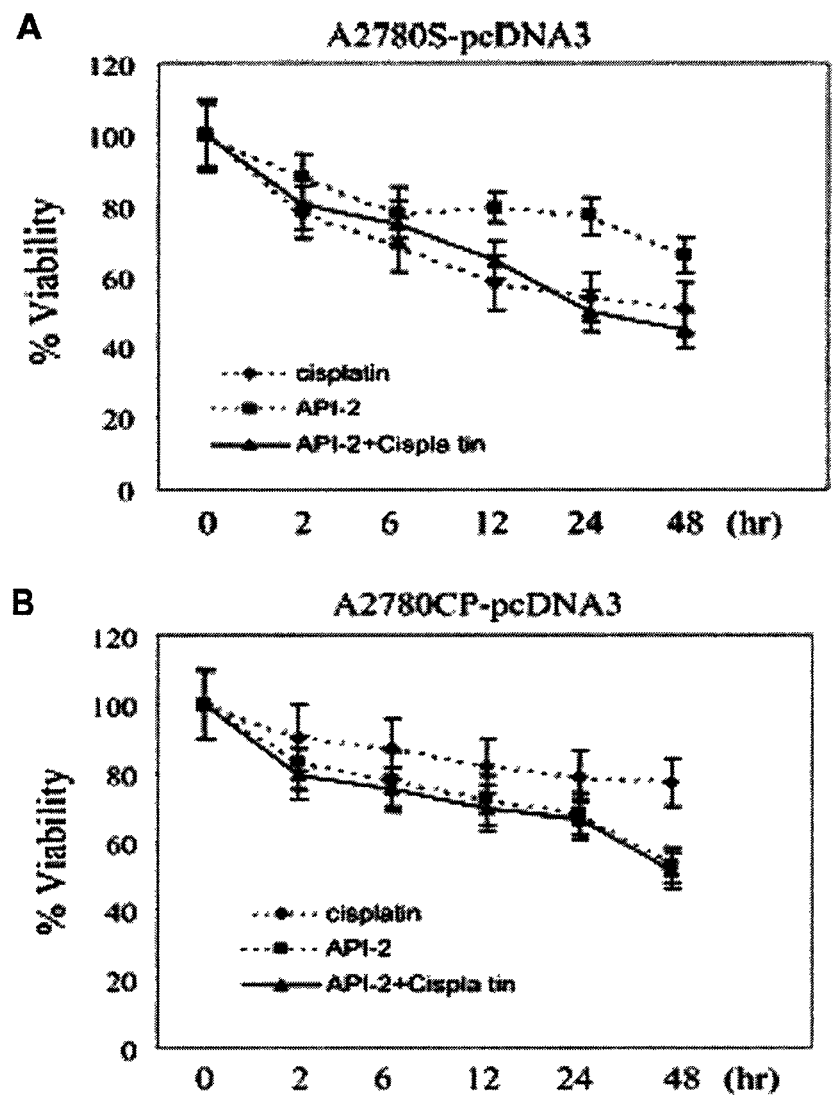

FIG. 38 shows cancer cells treated with combination treatment. (A) A2780S and (B) A2780CP cells were treated with 10 μM API-2, CDDP, or a combination of CDDP and API-2 for indicated times. Cells were assayed by MTT assay, showing API-2 overrides Aurora-A-induced CDDP resistance. Results represent the average of three runs. *p<0.05.

Figure 39:
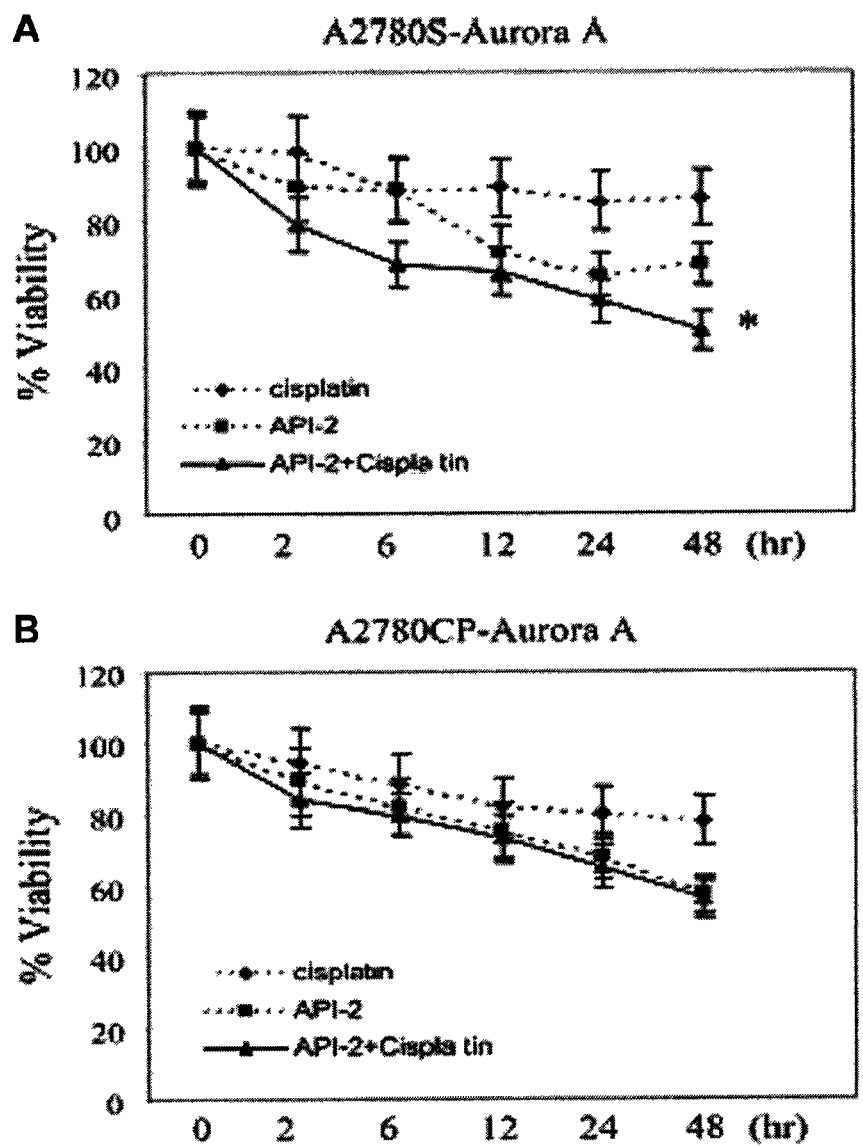

FIG. 39 shows cancer cells treated with combination treatment. (A) A2780S and (B) A2780CP cells were transfected with Aurora-A and treated with 10 μM API-2, CDDP, or a combination of CDDP and API-2 for indicated times. Cells were assayed by MTT assay, showing API-2 overrides Aurora-A-induced CDDP resistance. Results represent the average of three runs. *p<0.05.

Figure 40:
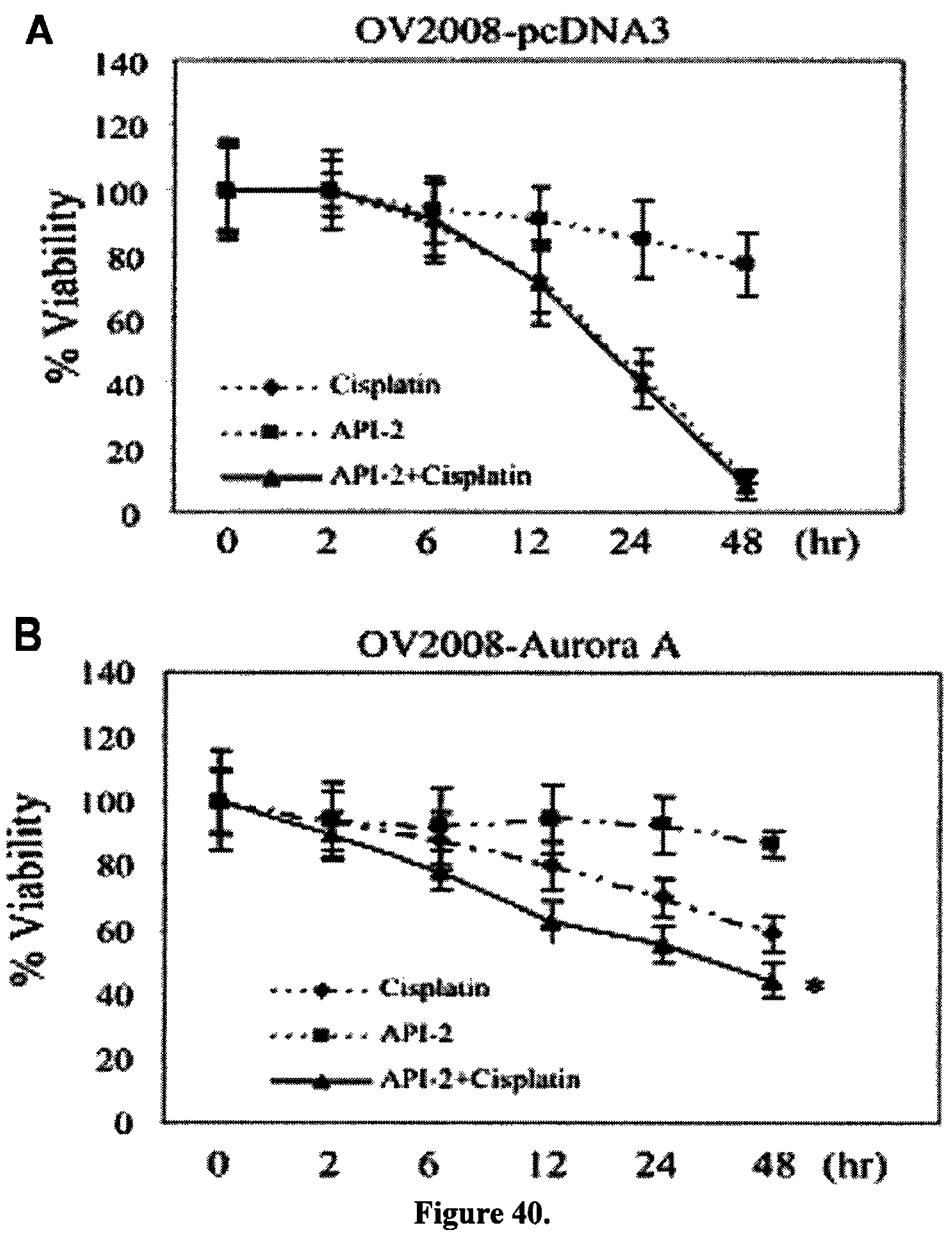

FIG. 40 shows Aurora-A transfected cancer cells. OV2008 cells, transfected with (A) control or (B) Aurora-A, were treated with 10 μM API-2, CDDP, or a combination of CDDP and API-2 for indicated times. Cells were assayed by MTT assay, showing API-2 overrides Aurora-A-induced CDDP resistance. Results represent the average of three runs. *p<0.05.

Figure 41:
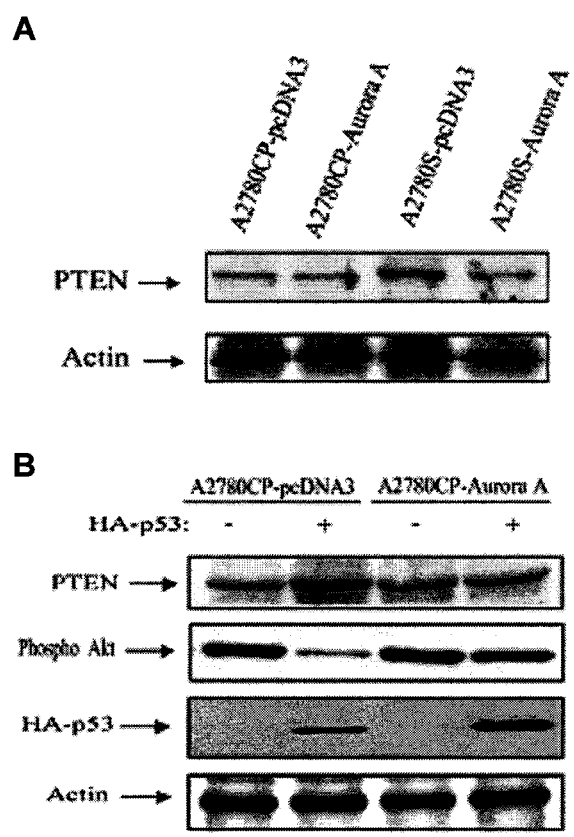

FIG. 41 depicts Aurora-A transfected cancer cells. (A) Aurora-A was introduced into A2780S and A2780CP cells and probed for apoptotic protein PTEN (top panel) or actin (bottom panel). Aurora-A inhibits PTEN expression in A2780S. (B) Cells were transfected with HA-p53 (+) or vector alone (−). 48 hr later, cells were lysed and immunoblotted with indicated antibodies. Reintroduction of wild-type p53 induced PTEN expression in A2780CP but not A2780CP-Aurora-A cells.

Figure 42:
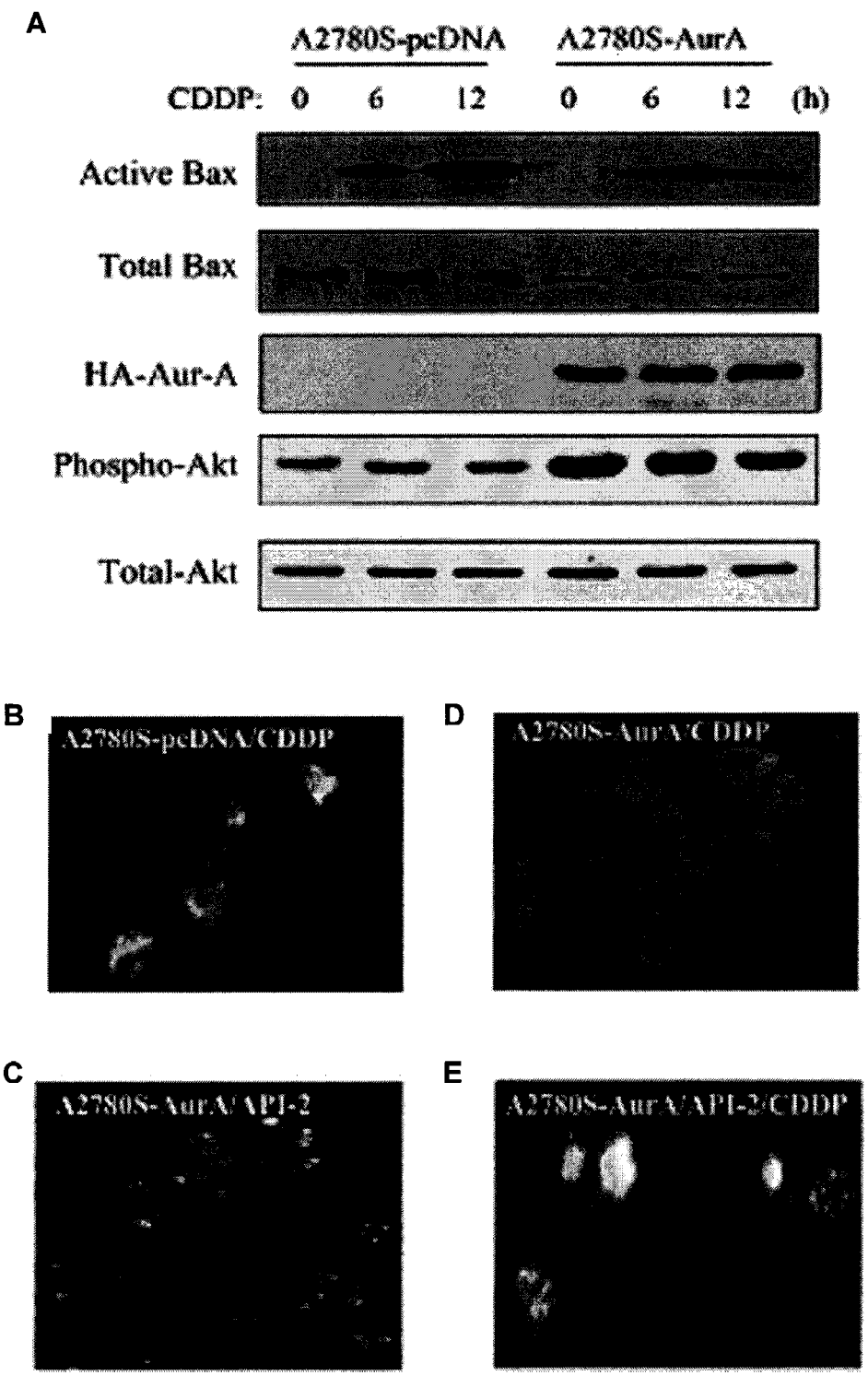

FIG. 42 depicts Aurora-A cancer cells after combination treatment. (A) A2780S cells were transfected with pcDNA or Aurora-A and treated with CDDP for indicated time points. Lysates were immunoprecipitated with anti-Bax 6A7 antibody and blotted with anti-Bax (total) antibody (top). Total cell lysates were immunoblotted with indicated antibodies. Due to Aurora-A inhibition of p53, total Bax protein was decreased in A2780S-Aurora-A cells, implying reduced Bax conformational from both activation of Akt and decreased Bax expression. (B-E) Aurora-A inhibits CDDP-induced mitochondrial translocation of Bax, which is overridden by Akt inhibitor API-2. A2780S cells were transfected with (B) pcDNA or (C, D, E) Aurora A. Cells were treated with (C) API-2, (D) CDDP or (E) a combination of API-2 and CDDP for 3 hr and stained with DAPI, MitoTracker (red), and anti-Bax (green) antibodies. Bax mitochondrial translocation was shown as white highlights.

Figure 43:
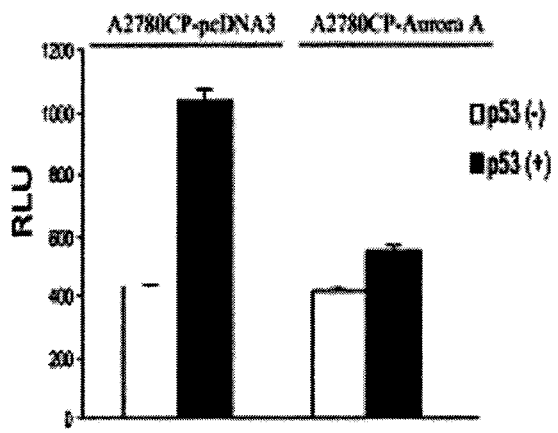

FIG. 43 depicts Aurora-A transfected cancer cells. Cells were transfected with PTEN-Luc with or without p53. 48 hr after transfection, cells were subjected to a luciferase reporter assay. Results showed activation of the PTEN promoter by p53 in A2780CP-pcDNA3 but not A2780CP-Aurora-A.

Figure 44:
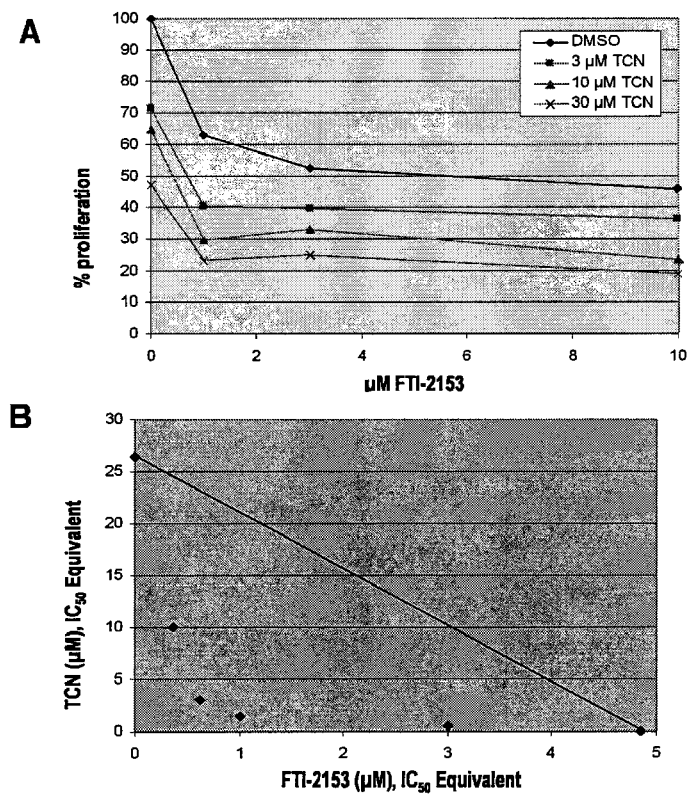

FIG. 44 depicts cancer cells after single or combination treatment. A549 cells were treated with TCN, farnesyltransferase inhibitor FTI-2153, or a combination of treatments as indicated for 72 hr. (A) Proliferation effects were assayed using tryptan blue exclusion. (B) Synergism was determined by plotting an isobologram using $IC_{50}$ equivalents for each drug alone, and then for each combination. Points falling below the $IC_{50}$ line for single treatments indicate synergistic combinations.

Figure 45:
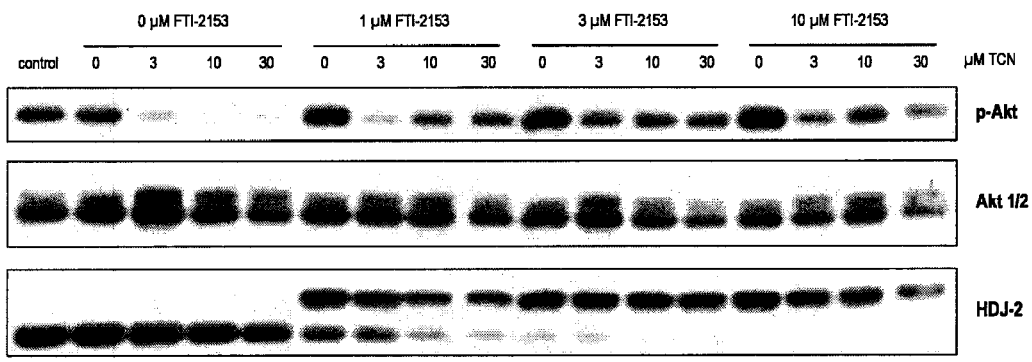

FIG. 45 depicts combination treatment results in a synergistic inhibition of tumor cell growth. A-549 cells were treated with TCN, FTI-2153, or both, as indicated for 72 hr. Cells were collected and lysed for Western blotting with p-Akt, Akt 1/2, p-ERK 1/2, p-S6K, Rap-1 and HDJ-2 antibodies.

Figure 46:
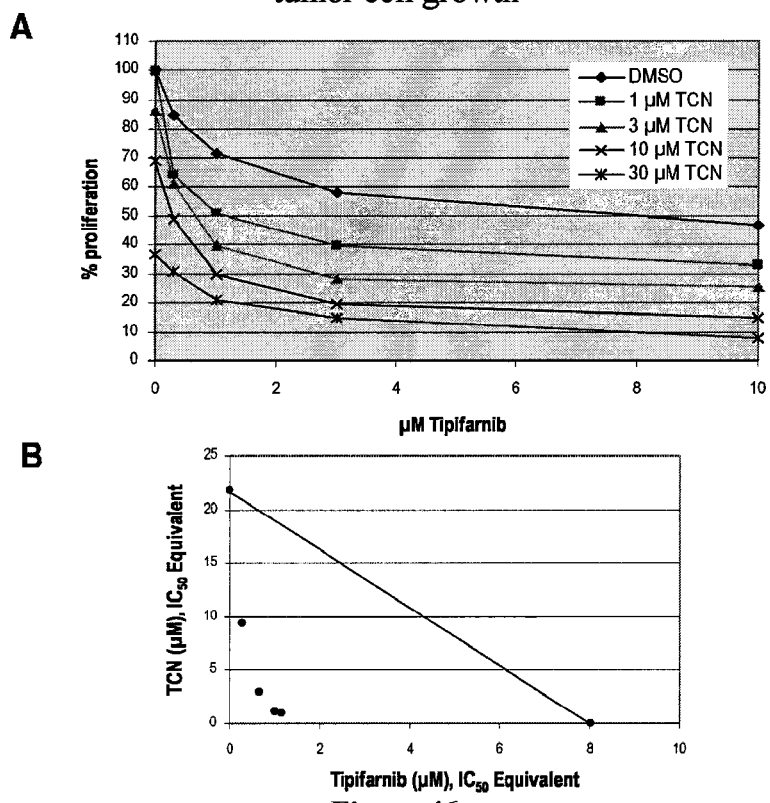

FIG. 46 depicts combination treatment results in a synergistic inhibition of tumor cell growth. A549 cells were treated with TCN and/or Tipifarnib as indicated for 72 hr. Proliferation effects (A) were assessed by MTT assay. Synergism was determined by plotting an isobologram using $IC_{50}$ equivalents (B) for each drug alone, and then each combination. Points falling below the $IC_{50}$ line for single treatments indicate synergistic combinations.

Figure 47:
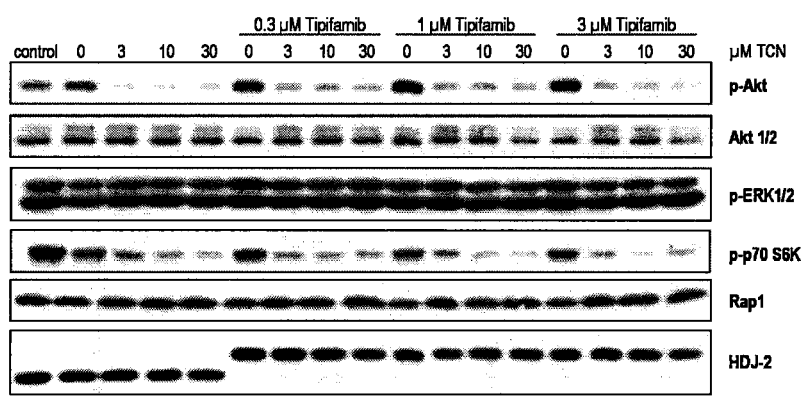

FIG. 47 depicts combination treatment results in a synergistic inhibition of tumor cell growth. A-549 cells were treated with TCN, Tipifarnib, or both, as indicated for 72 hr. Cells were collected and lysed for Western blotting with p-Akt, Akt 1/2, p-ERK 1/2, p-S6K, Rap-1 and HDJ-2 antibodies.

Figure 48:
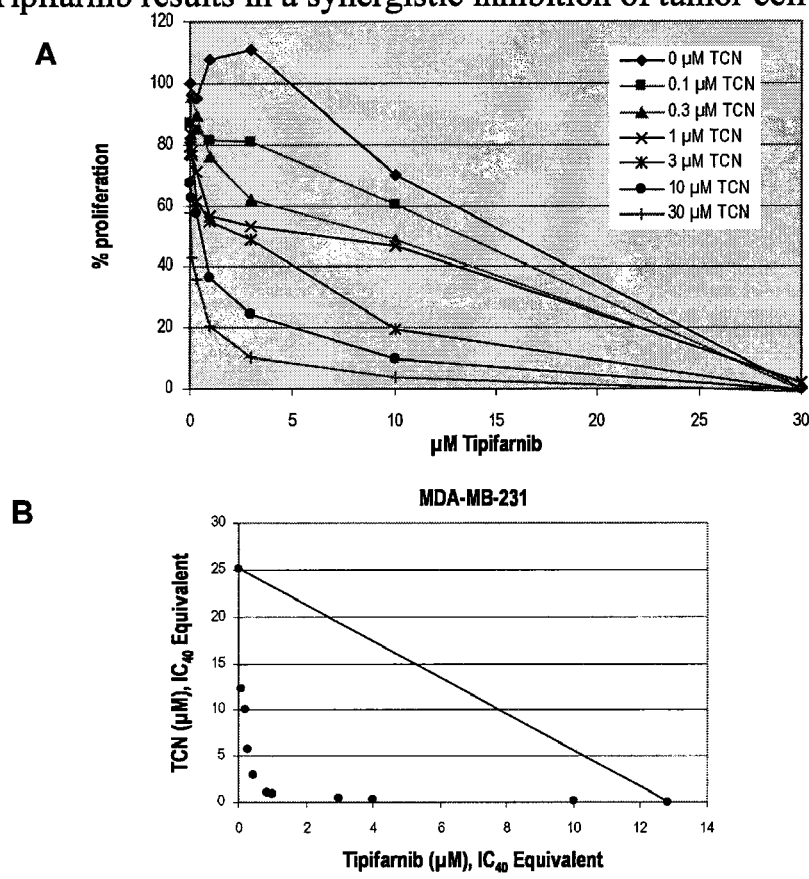

FIG. 48 depicts combination treatment results in a synergistic inhibition of tumor cell growth. MDA-MB-231 cells were treated with TCN and/or Tipifarnib as indicated for 72 hr. (A) Proliferation effects were assessed by MTT assay. (B) Synergism was determined by plotting an isobologram using $IC_{50}$ equivalents for each drug alone, and then each combination. Points falling below the $IC_{50}$ line for single treatments indicate synergistic combinations.

Figure 49:
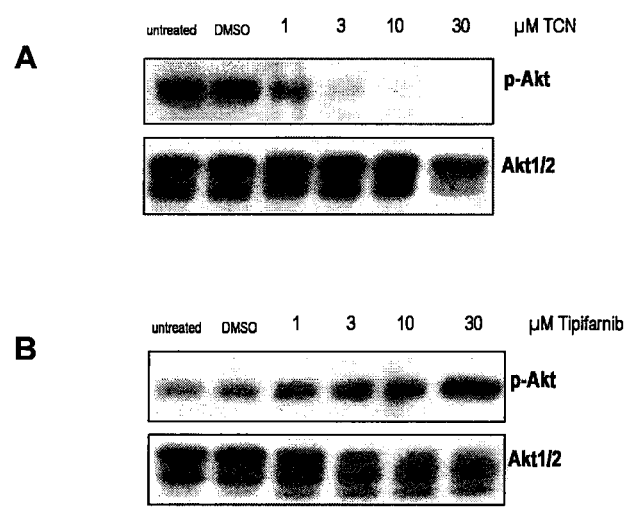

FIG. 49 depicts combination treatment results in a synergistic inhibition of tumor cell growth. MDA-MB-231 cells were treated with (A) TCN or (B) Tipifarnib as indicated for 72 hr. Cells were collected and lysed for Western blotting with p-Akt and Akt 1/2 antibodies.

Figure 50:
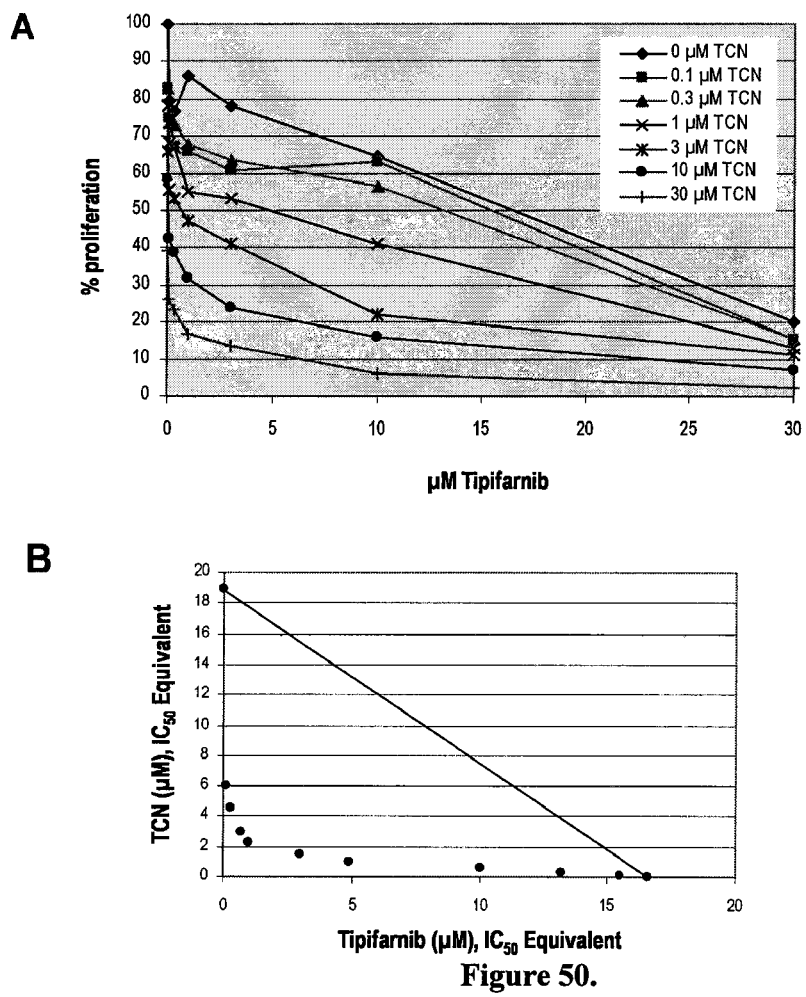

FIG. 50 depicts combination treatment results in a synergistic inhibition of tumor cell growth. MCF-7 cells were treated with TCN and/or Tipifarnib as indicated for 72 hr. (A) Proliferation effects were assessed by MTT assay. (B) Synergism was determined by plotting an isobologram using $IC_{50}$ equivalents for each drug alone, and then each combination. Points falling below the $IC_{50}$ line for single treatments indicate synergistic combinations.

Figure 51:
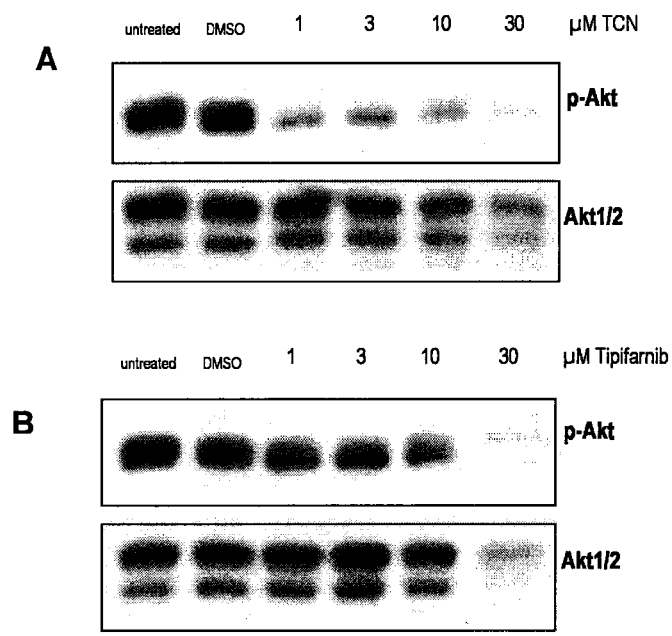

FIG. 51 depicts combination treatment results in a synergistic inhibition of tumor cell growth. MCF-7 cells were treated with (A) TCN or (B) Tipifarnib as indicated for 72 hr. Cells were collected and lysed for Western blotting with p-Akt and Akt 1/2 antibodies.

Figure 52:
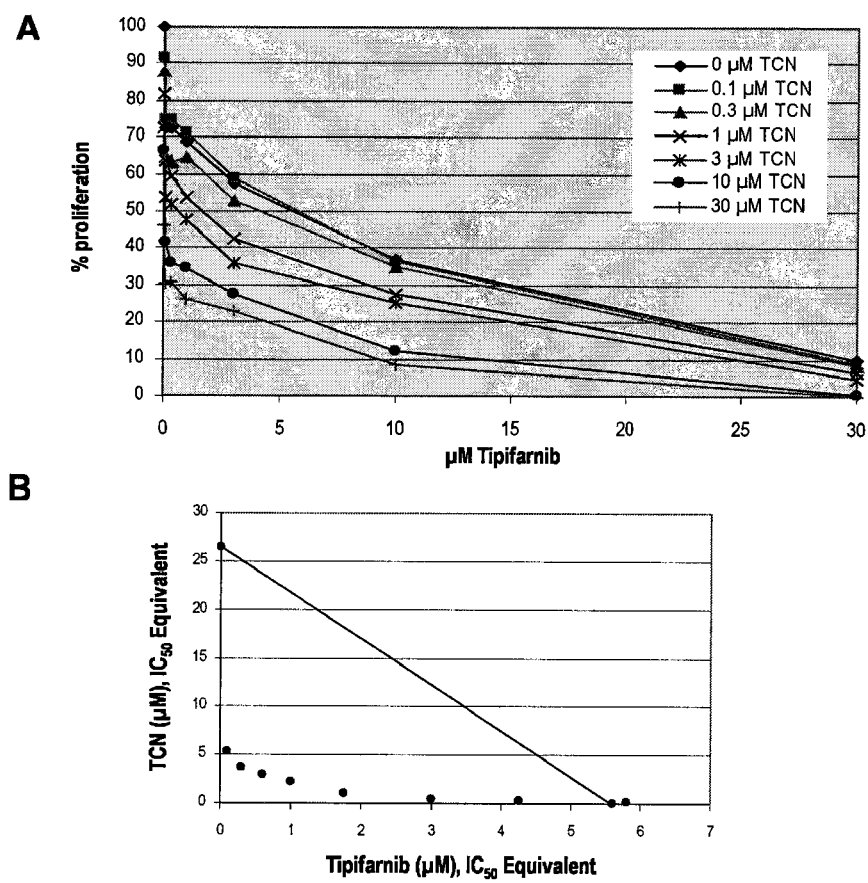

FIG. 52 depicts combination treatment results in a synergistic inhibition of tumor cell growth. U266 cells were treated with TCN and/or Tipifarnib as indicated for 72 hr. (A) Proliferation effects were assessed by MTT assay. (B) Synergism was determined by plotting an isobologram using $IC_{50}$ equivalents for each drug alone, and then each combination. Points falling below the $IC_{50}$ line for single treatments indicate synergistic combinations.

Figure 53:
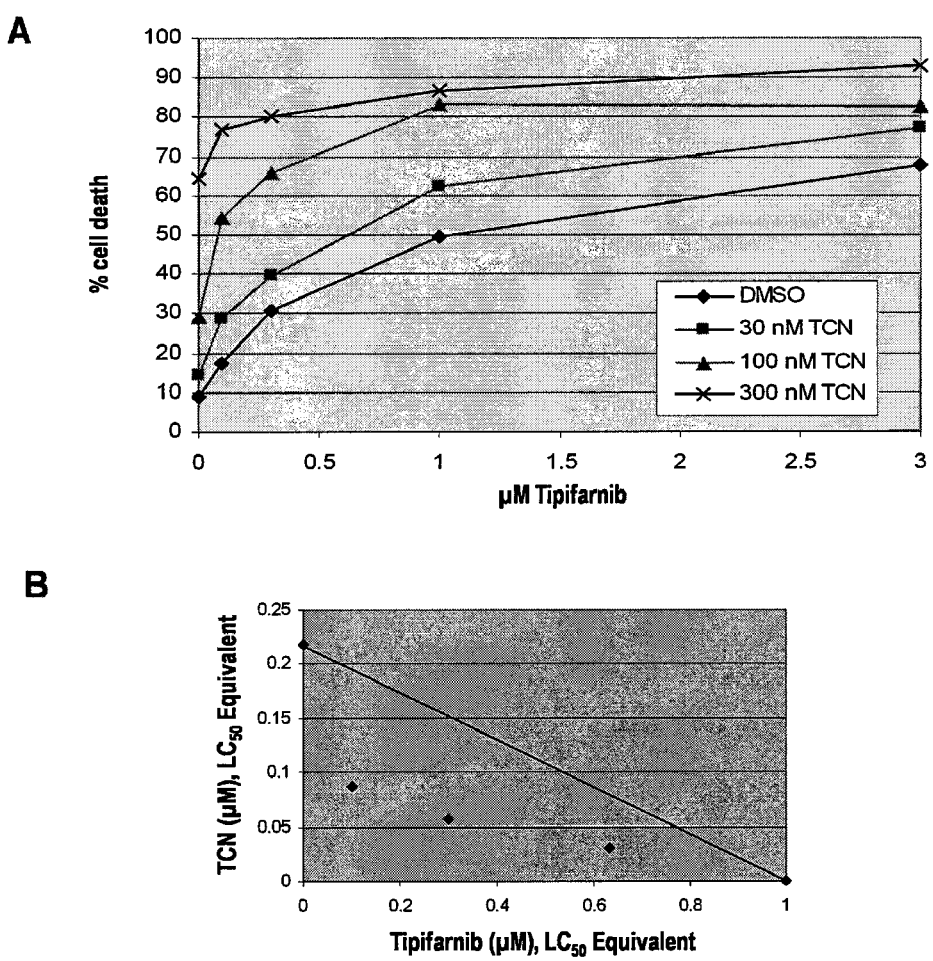

FIG. 53 depicts combination treatment results in a synergistic inhibition of tumor cell growth. MV4-11 cells were treated with TCN and/or Tipifarnib as indicated for 72 hr. (A) Cytotoxic effects were assessed by trypan blue exclusion. (B) Synergism was determined by plotting an isobologram using $LC_{50}$ equivalents for each drug alone, and then each combination. Points falling below the $IC_{50}$ line for single treatments indicate synergistic combinations.

Figure 54:
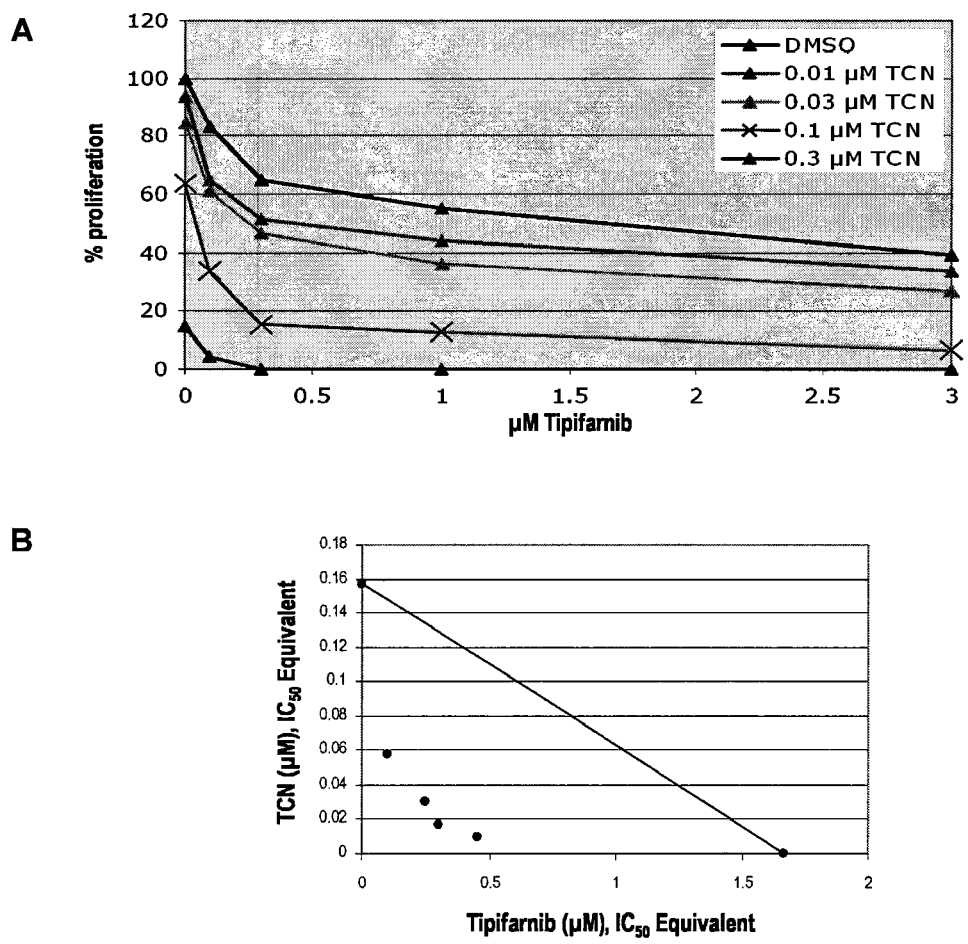

FIG. 54 depicts combination treatment results in a synergistic inhibition of tumor cell growth. MV4-11 cells were treated with TCN and/or Tipifarnib as indicated for 72 hr. (A) Proliferation effects were assessed by MTT assay. (B) Synergism was determined by plotting an isobologram using $IC_{50}$ equivalents for each drug alone, and then each combination. Points falling below the $IC_{50}$ line for single treatments indicate synergistic combinations.

FIG. 55 depicts combination treatment results in a synergistic inhibition of tumor cell growth. MV4-11 cells were treated with (A) TCN or (B) Tipifarnib as indicated for 72 hr. Cells were collected and lysed for Western blotting with p-Akt, Akt 1/2, HDJ-2, Rap-1 and β-actin antibodies.

FIG. 56 depicts combination treatment results in a synergistic inhibition of tumor cell growth. HL-60 cells were treated with TCN and/or Tipifarnib as indicated for 72 hr. (A) Cytotoxic effects were assessed by trypan blue exclusion. (B) Synergism was determined by plotting an isobologram using $LC_{50}$ equivalents for each drug alone, and then each combination. Points falling below the $IC_{50}$ line for single treatments indicate synergistic combinations.

Figure 57:
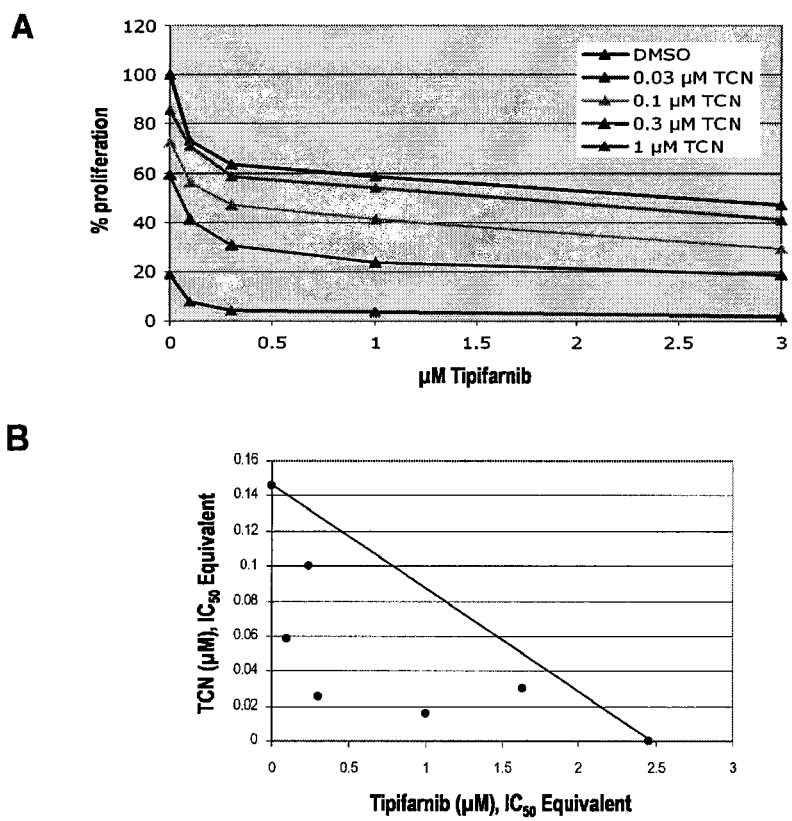

FIG. 57 depicts combination treatment results in a synergistic inhibition of tumor cell growth. HL-60 cells were treated with TCN and/or Tipifarnib as indicated for 72 hr. (A) Proliferation effects were assessed by MTT assay. (B) Synergism was determined by plotting an isobologram using $IC_{50}$ equivalents for each drug alone, and then each combination. Points falling below the $IC_{50}$ line for single treatments indicate synergistic combinations.

Figure 58:
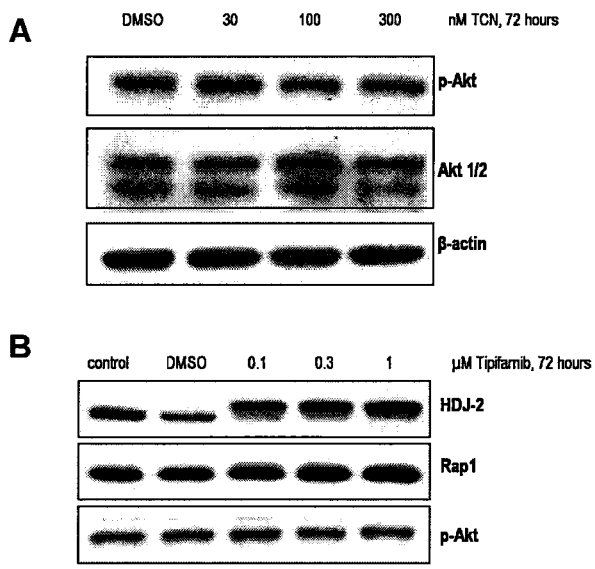

FIG. 58 depicts combination treatment results in a synergistic inhibition of tumor cell growth. HL-60 cells were treated with (A) TCN or (B) Tipifarnib as indicated for 72 hr. Cells were collected and lysed for Western blotting with p-Akt, Akt 1/2, HDJ-2, Rap-1 and β-actin antibodies.

Figure 59:
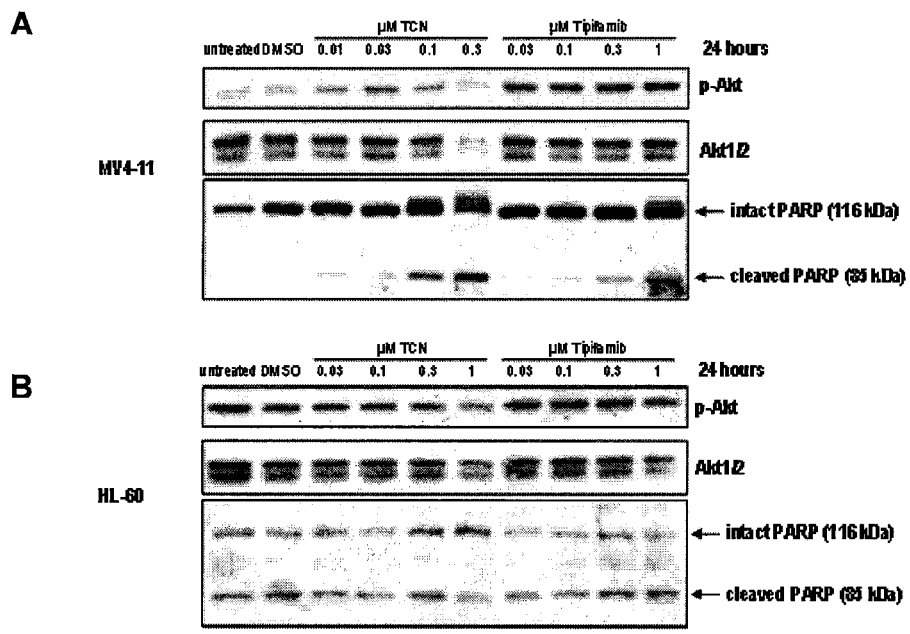

FIG. 59 depicts the effect of treatment of TCN or farnesyltransferase inhibitor. (A) MV4-11 and (B) HL-60 cells were treated with TCN or Tipifarnib as indicated for 24 hr. Cells were collected and lysed for Western blotting with p-Akt, Akt 1/2, and PARP antibodies.

Figure 60:
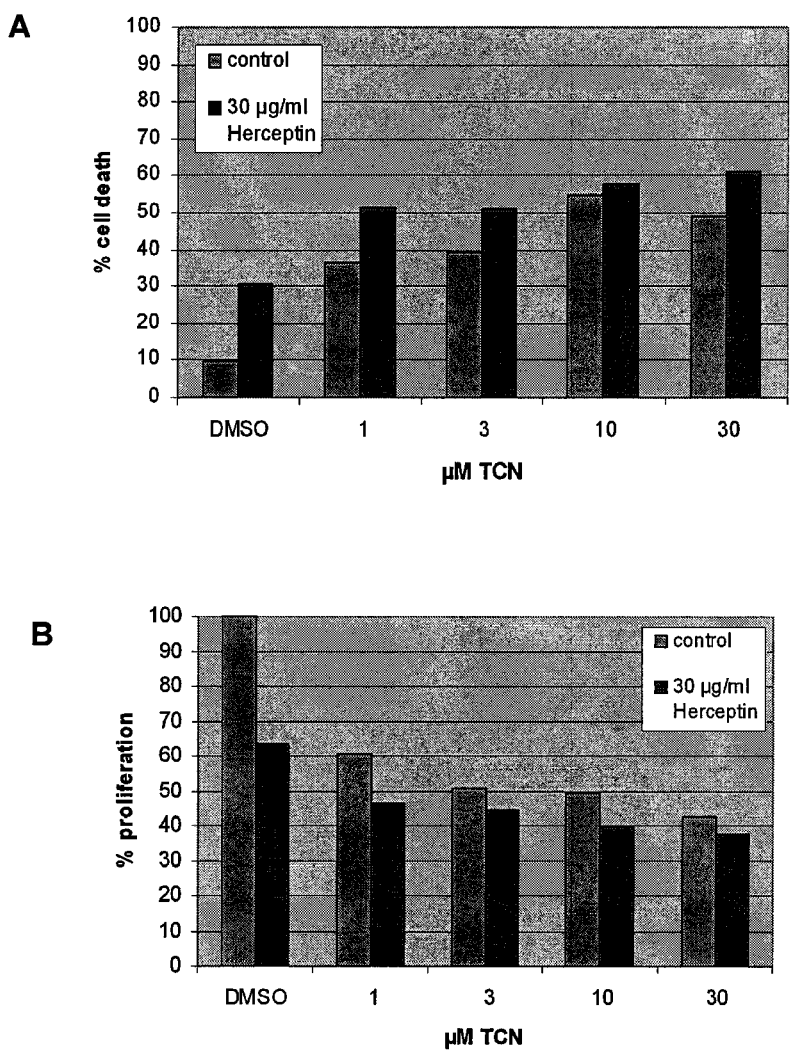

FIG. 60 depicts cancer cell reaction after treatment with varying doses of TCN or HER-2 inhibitor. SK-Br-3 cells were treated with increasing doses of TCN, with and without 30 µg/ml Herceptin, for 72 hr. (A) Cell death and (B) proliferation were assessed by trypan blue exclusion. Treated cells were collected and lysed for Western blotting with ErbB2 and p-Akt antibodies.

Figure 61:
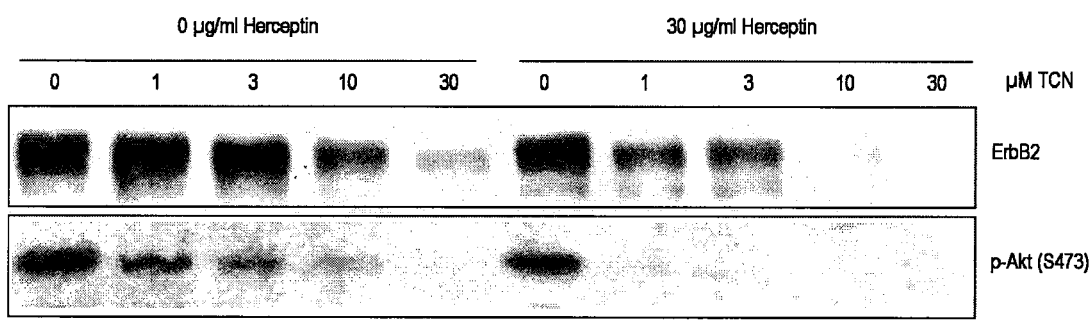

FIG. 61 depicts SK-Br-3 cells were treated with increasing doses of TCN, with and without 30 µg/ml Herceptin, for 72hr. Treated cells were collected and lysed for Western blotting with ErbB2 and p-Akt antibodies.

DETAILED DESCRIPTION OF THE PREFERRED EMBODIMENT

The present invention provides a method of treating cancer with coadministration of Akt inhibitor and a traditional anti-cancer drug. In particular, the invention provides for using an effective amount of Triciribine (TCN), also known as Akt/PKB inhibitor-2 (API-2), or Triciribine phosphate (TCNP) with an effective amount of an anticancer drug, such as cisplatin, taxane, farnesyltransferase inhibitor, geranylgeranyltransferase inhibitor, rapamycin, RAD001, U0126, Herceptin, or Erbitux.

A therapeutically effective amount is defined as a quantity of compound sufficient to yield a desired therapeutic response.

Akt has been shown to up-regulate, sometimes drastically, in tumor masses during chemotherapeutic or radiotherapeutic treatment. The tumor masses become highly resistant to further treatment, producing the belief that Akt is involved in tumor chemoresistance and radioresistance. To determine the effect of treating tumor cells with anti-neoplastic agent and Akt inhibitor, p53 wild-type (A2780S, OV2008, C-13, A549, MCF-7) and p53 null (A2780CP, MDA-MB-435, OVCAR-3, DU-145, U266, HL60, SkBr3) cell lines were treated with varying anti-neoplastic agents alone or in combination with Akt inhibitors TCN, TCN-P, and API-2.

Figure 1:
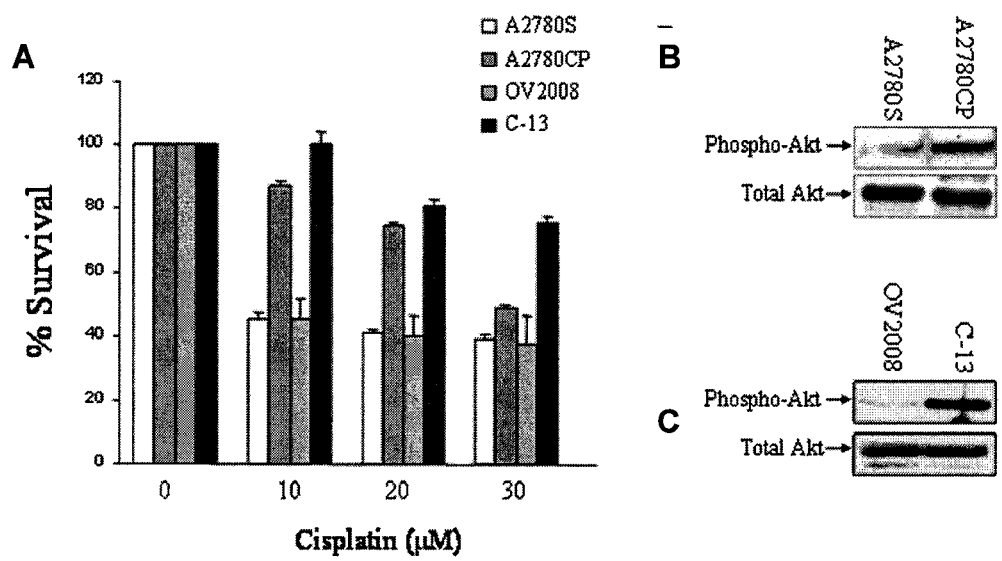
FIG. 1 shows survival percentages and Akt protein levels of cancer cell lines. Human ovarian cancer cell lines A2780S, A2780CP, OV2008, and C-13 were treated with CDDP at the indicated concentrations. (A) Cell survival was assayed 24 hr afterwards using MTT assay. (B, C) Cells were lysed and Western Blotted with anti-phosphoSer473-Akt and total Akt antibodies.
Figure 2:
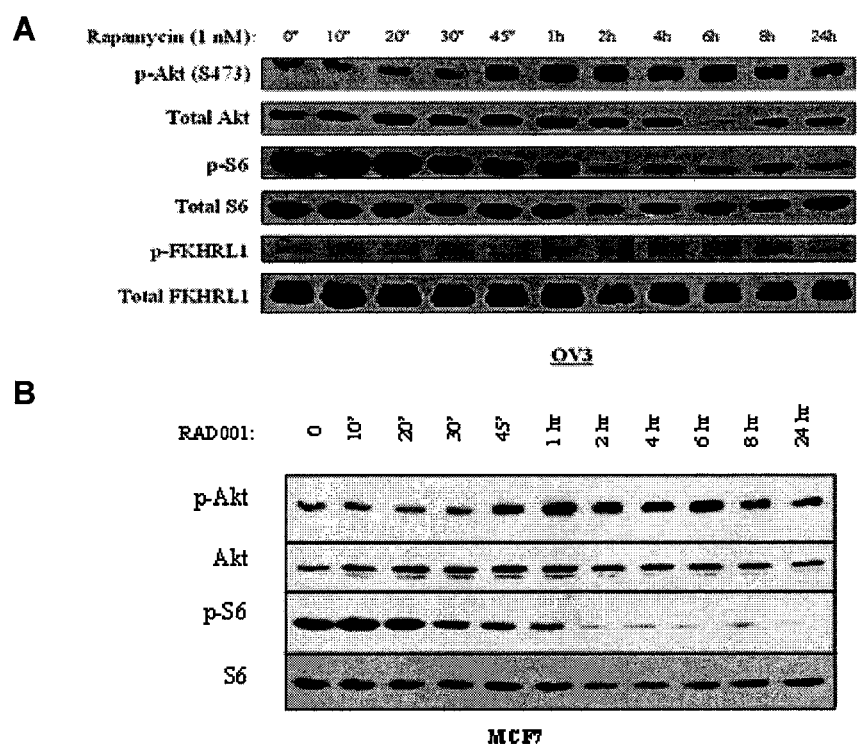
FIG. 2 shows protein levels in cancer cell lines after mTOR inhibition. (A) OVCAR-3 human ovarian cancer and (B) MCF-7 human breast cancer cell lines were treated with mTOR inhibitors rapamycin (OVCAR-3 cells only) or RAD001 (MCF-7 cells only). Cell lysates were probed for phosphorylated and total Akt, and phosphorylated and total S6 at the indicated time points. While total Akt and S6 levels remained constant, phosphorylated Akt increased with longer exposure time whereas phosphorylated S6 decreased with exposure. Akt substrate FKHRL1, an apoptotic protein, was also detected.

To confirm tumor cell reliance on Akt in overcoming chemotherapy and radiotherapy, p53 wild-type (A2780S, OV2008, C-13) and p53 null (A2780CP) cell lines were treated with cis-Diammine-dichloroplatinum II (CDDP), as chemotherapy has been shown to activate an Akt-dependent survival pathway. After CDDP treatment, C-13 and A2780CP exhibited higher survivability than A2780S and OV2008, as shown in FIGS. 1A through 1C. Results of Western Blot for phosphorylated Akt (p-Akt) indicate C-13 and A2780CP cells had high levels of p-Akt. Further, cell survivability after chemotherapy appears directly connected to Akt up-regulation as C-13 had both the highest p-Akt and survivability. Further, as shown in FIGS. 2A and 2B, cells were treated with a mammalian target of rapamycin (mTOR) inhibitor. This caused an increase in p-Akt within 1 hour of treatment, confirming a relationship between p-Akt and cell survival after chemotherapy.

Figure 3:
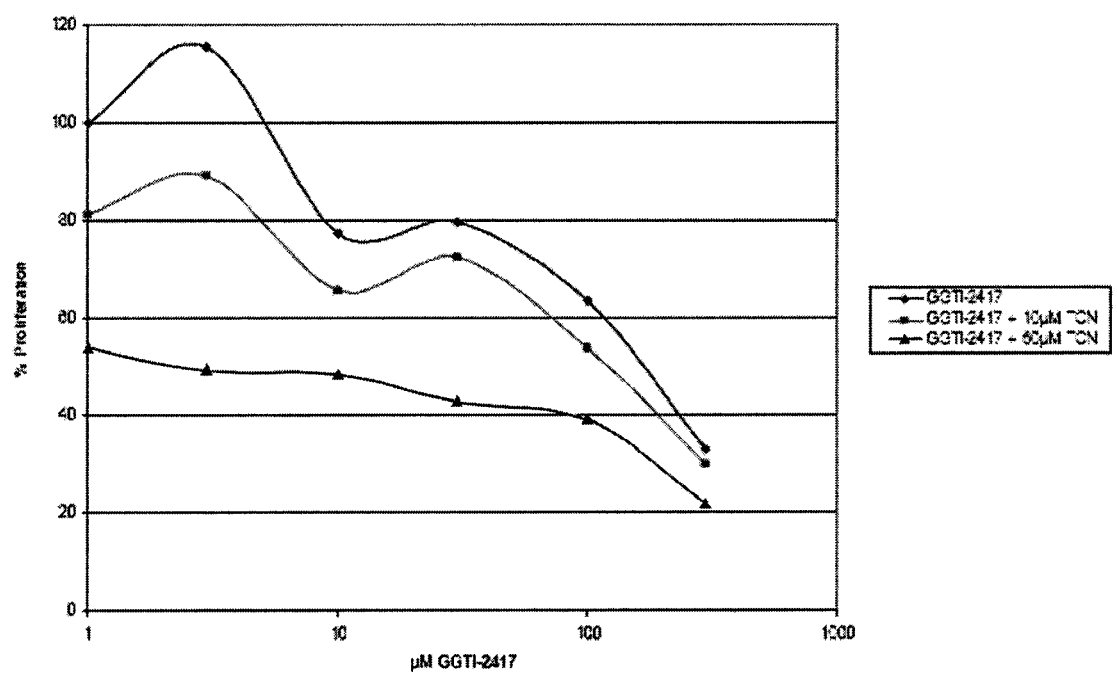
FIG. 3 shows a graph of A-549 human lung cancer cell line proliferation after 72 hr combination treatment of TCN and geranylgeranyltransferase I inhibitor, GGTI-2417.
Figure 4:
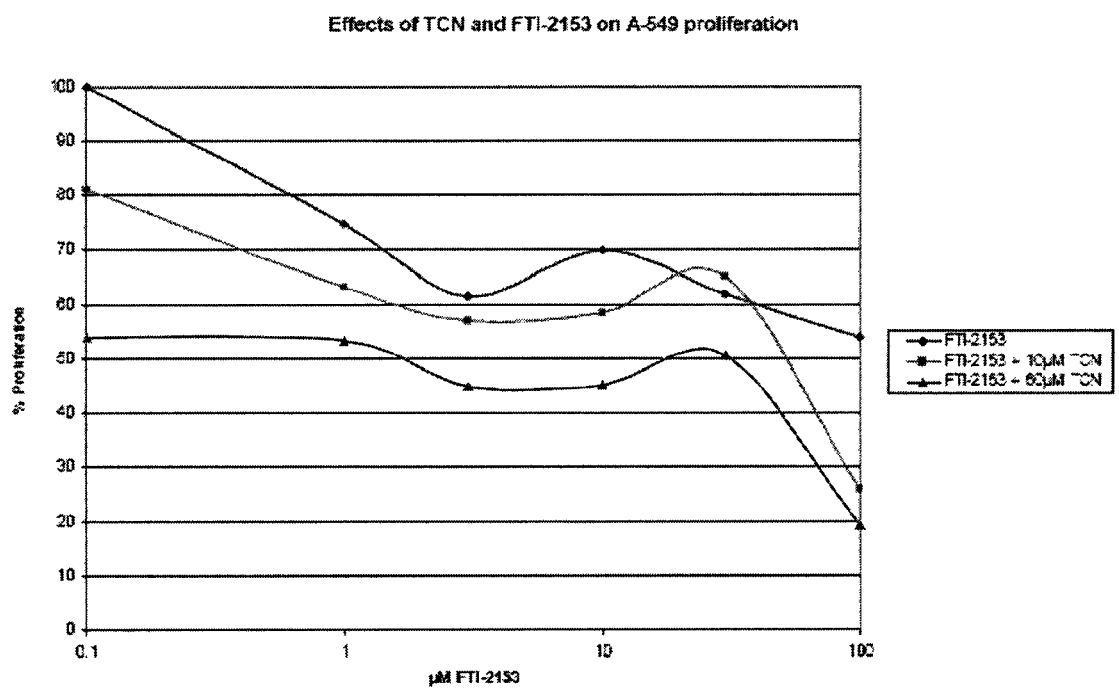
FIG. 4 depicts a graph of A-549 human lung cancer cell line proliferation after 72 hr combination treatment with TCN and farnesyltransferase inhibitor, FTI-2153.
Figure 5:
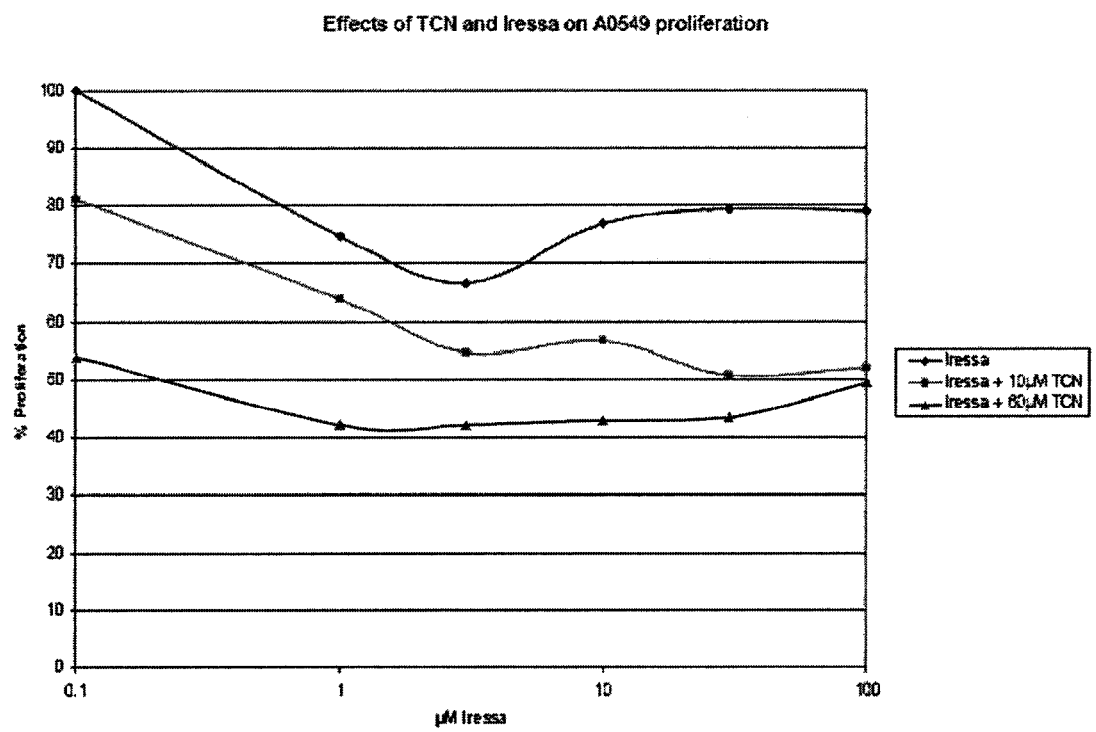
FIG. 5 shows a graph of A-549 human lung cancer cell line proliferation after 72 hr combination treatment with TCN and epidermal growth factor receptor tyrosine kinase inhibitor, Iressa.
Figure 6:
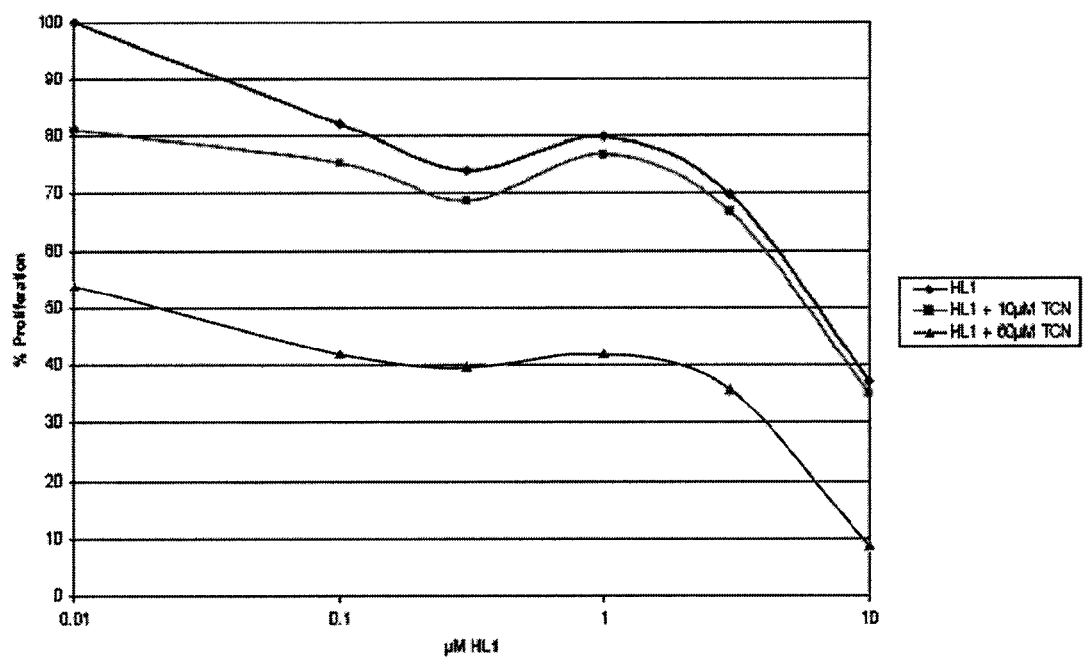
FIG. 6 shows a graph of A-549 human lung cancer cell line proliferation after 72 hr combination treatment with TCN and proteosome inhibitor, HL-1.
Figure 7:
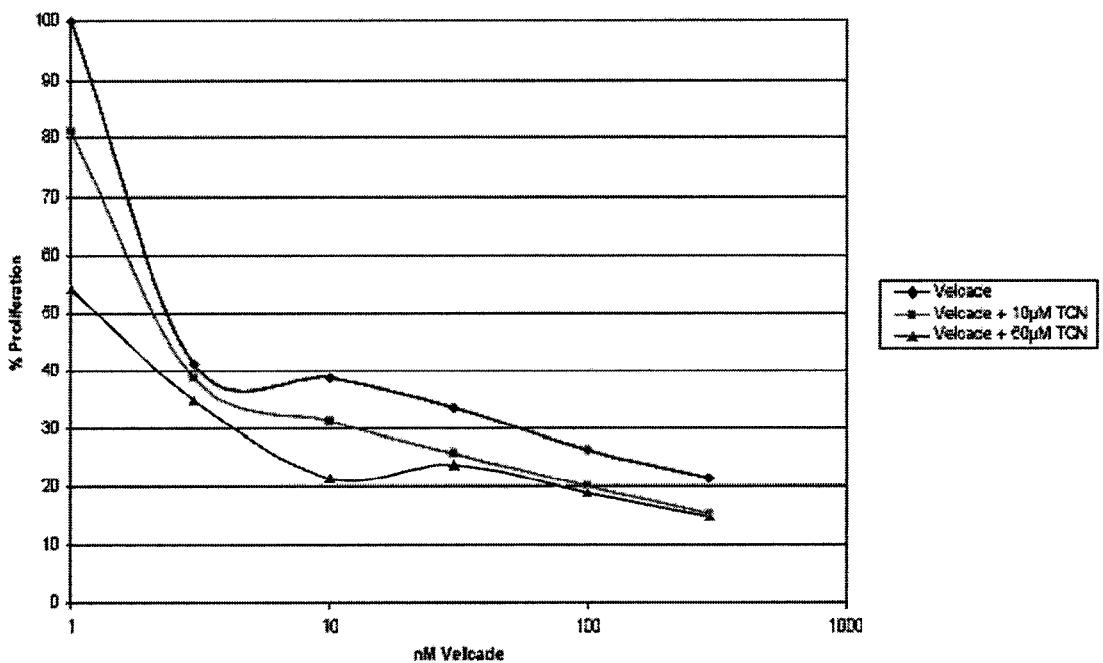
FIG. 7 shows a graph of A-549 human lung cancer cell line proliferation after 72 hr combination treatment with TCN and proteosome inhibitor, Velcade.
Figure 8:
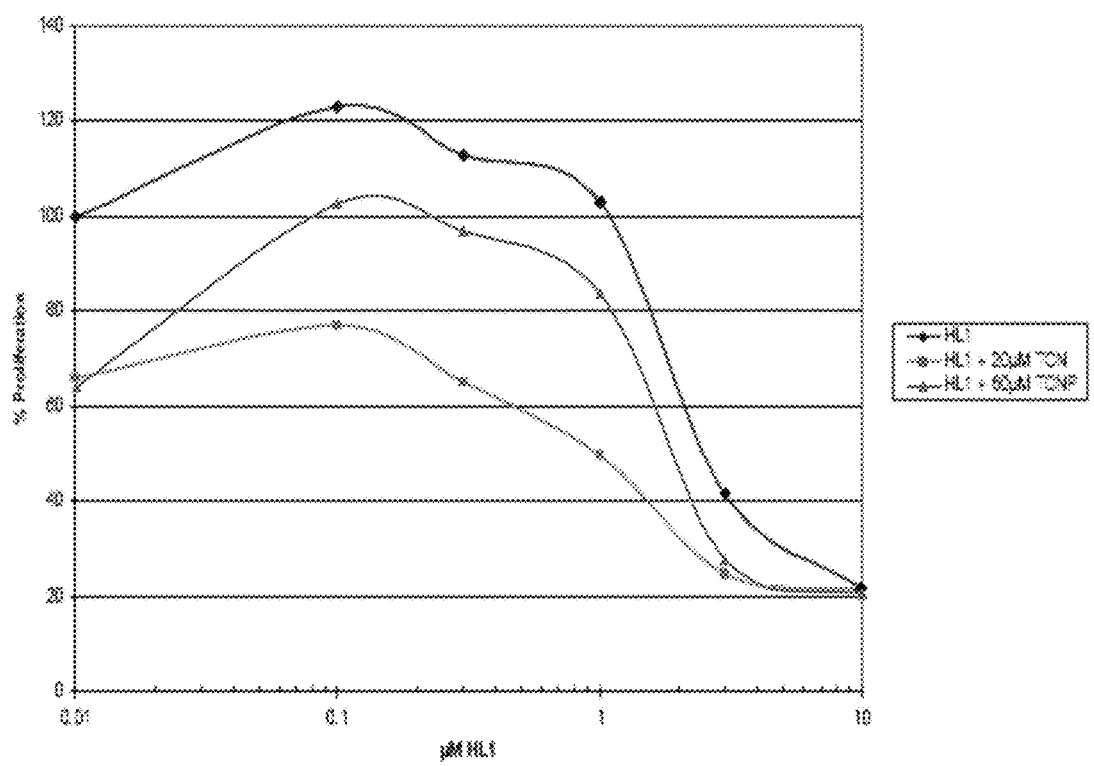
FIG. 8 shows a graph of A-549 human lung cancer cell line proliferation after 72 hr combination treatment with TCN and proteosome inhibitor, HL-1.
Figure 9:
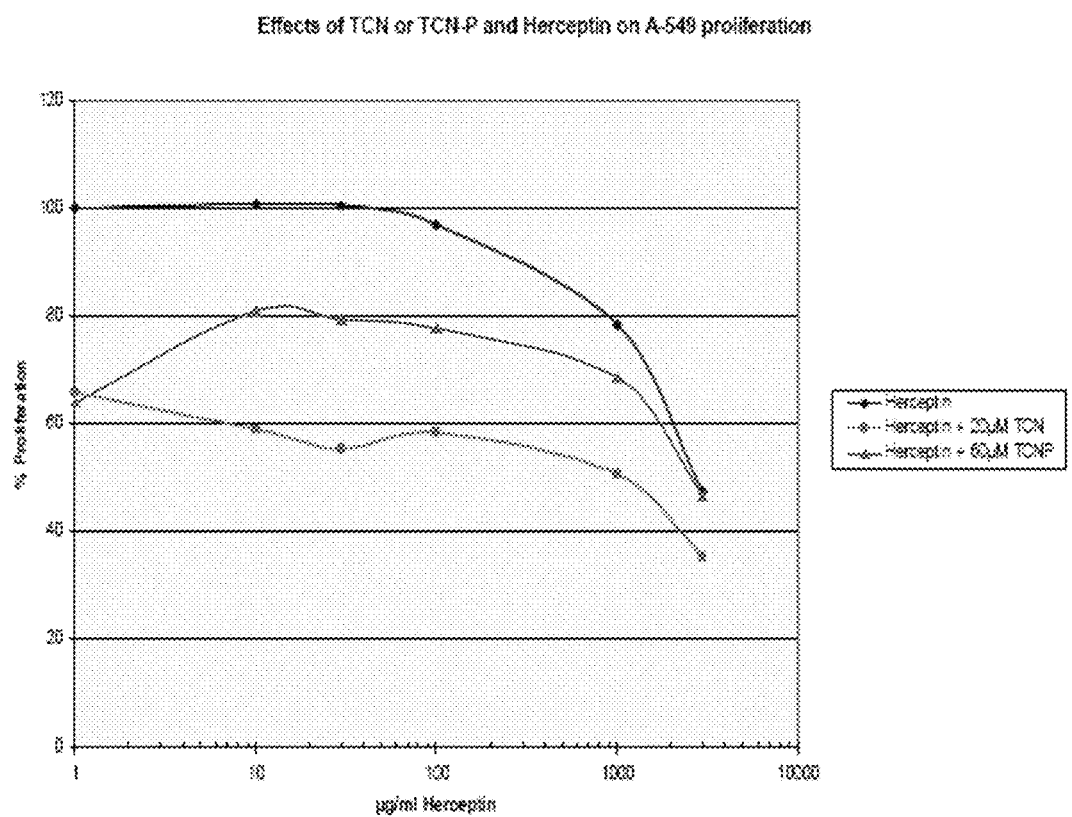
FIG. 9 shows a graph of A-549 human lung cancer cell line proliferation after 72 hr combination treatment with TCN or TCN-P and 30 μg/ml HER2 blocker, Herceptin.
Figure 10:
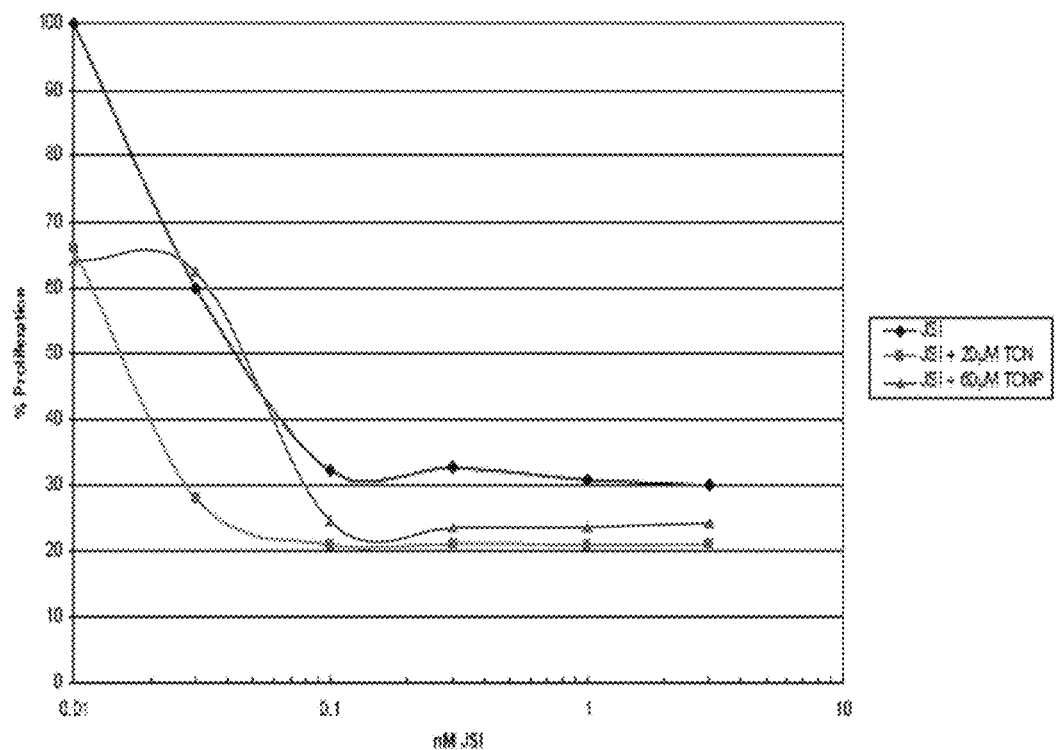
FIG. 10 shows a graph of A-549 human lung cancer cell line proliferation after 72 hr combination treatment with TCN or TCN-P and the JAK2/STAT3 inhibitor, JSI-124.
Figure 11:
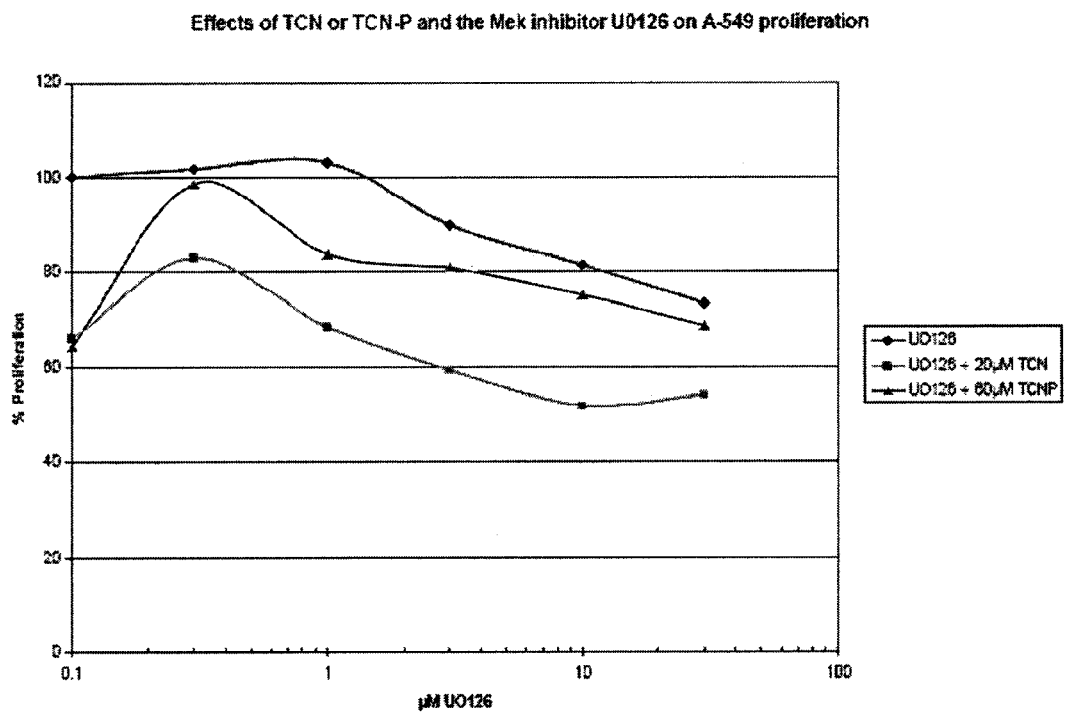
FIG. 11 shows a graph of A-549 human lung cancer cell line proliferation after 72 hr combination treatment with TCN or TCN-P and the Mek inhibitor, U0126.

The effect of Akt inhibition on chemotherapeutic cancer treatment was determined through analyzing p53 wild-type A-549 cells treated with 9 different anti-neoplastic agents at varying concentrations. Cell proliferation data was collected and compared to concentration levels of anti-neoplastic agent. The cells were treated with transferase inhibitor agents with or without TCN, seen in FIGS. 3 through 5. The addition of TCN has an additive or synergistic effect, with higher TCN concentrations further increasing the inhibitory effectiveness. Cells were treated with a proteasome inhibitor, shown in FIGS. 6 to 8. TCN increases the inhibitory effect, however higher levels of TCN have less clear cut results. The cells were then treated with anti-signaling agents alone or in combination with TCN or TCN-P, shown in FIGS. 9 to 11, with similar results.

Figure 12:
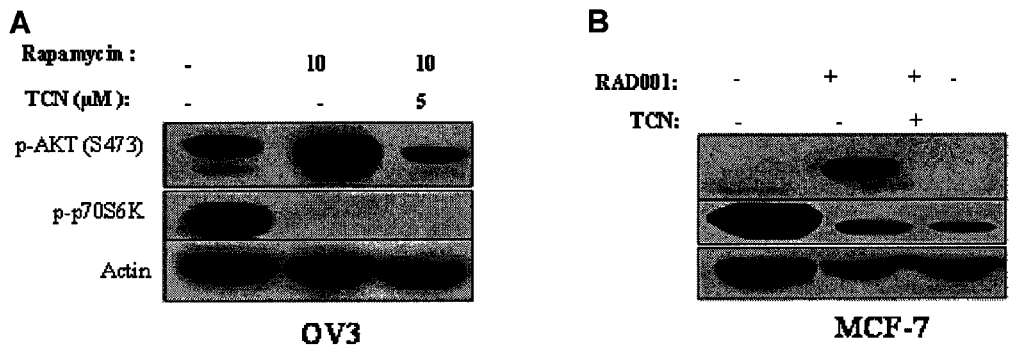
FIG. 12 shows cancer cells treated with a combination treatment. (A) OVCAR-3 and (B) MCF-7 cells were treated with rapamycin (OVCAR-3 cells only), RAD001 (MCF-7 cells only), API-2, or a combination of API-2 with either rapamycin or RAD001. Akt phosphorylation increased in both cell lines after either rapamycin or RAD001 treatment. However, a combination treatment or API-2 with either rapamycin or RAD001 caused Akt phosphorylation to fall at or below basal phosphorylated Akt levels. Phosphorylation of p70-S6K also decreased with the combination treatment.
Figure 14:
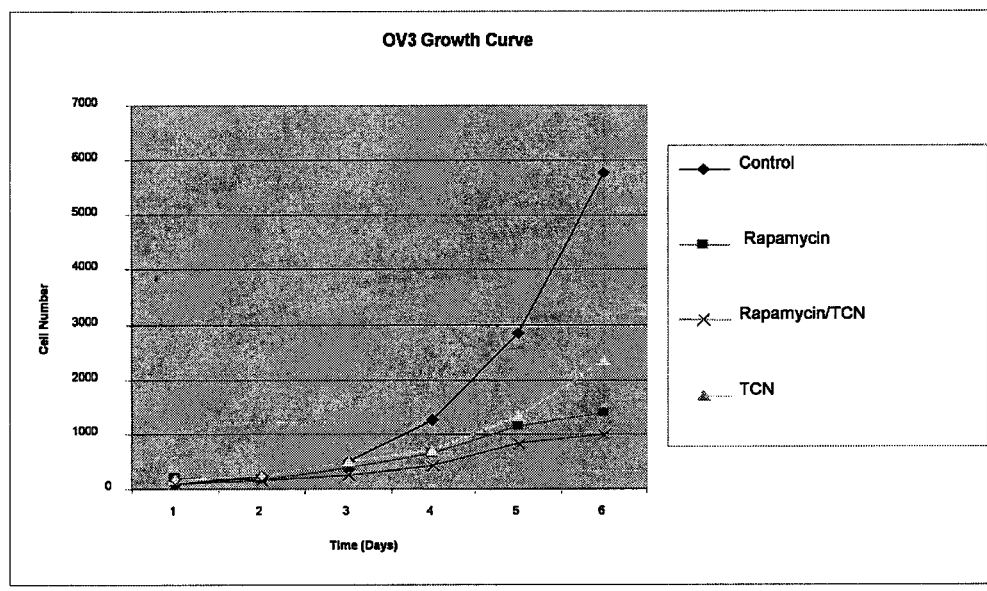
FIG. 14 depicts the inhibition of cell growth after combination treatment of TOR inhibitor with API-2 (TCN). OVCAR-3 human ovarian cancer cells were treated with 1 nM rapamycin, 5 μM API-2, or a combination of API-2 with rapamycin. Cell numbers were measured for six days after treatment. Rapamycin inhibited cell growth, while TCN provided a similar inhibitory effect of cell numbers. However, cell growth was further inhibited by combination treatment.

OVCAR-3, MCF-7, and DU-146 cells were treated with mTOR inhibitors, rapamycin or RAD001, alone or in combination with TCN. Cell lysates were taken and probed for p-Akt, phosphorylated rapamycin target serine/threonine kinase p70S6K, and actin. mTOR inhibitor treatment activates Akt and eliminates phosphorylated p70S6K, as seen in FIGS. 12A and 12B. However, the addition of TCN prevents activation of Akt and inhibits the growth of cancer cells, even beyond mTOR inhibition treatment alone, shown in FIGS. 13A through 14.

Figure 15:
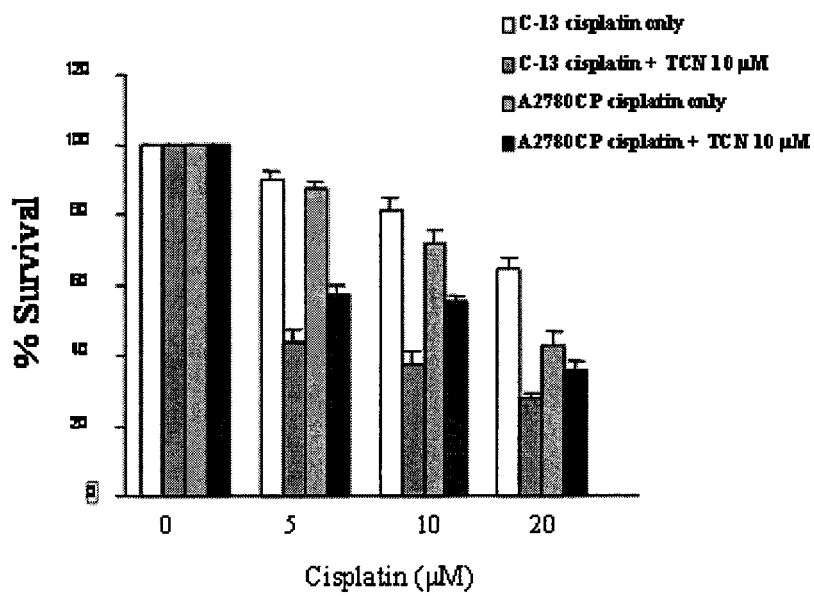
FIG. 15 depicts the cell survival of CDDP-resistant ovarian cells after treatment. CDDP-resistant ovarian cancer cell lines A2780CP and C-13 were treated with CDDP at indicated concentrations alone, or in combination with 10 μM API-2. Cell survival was determined 24 hr later by MTT assay.
Figure 16:
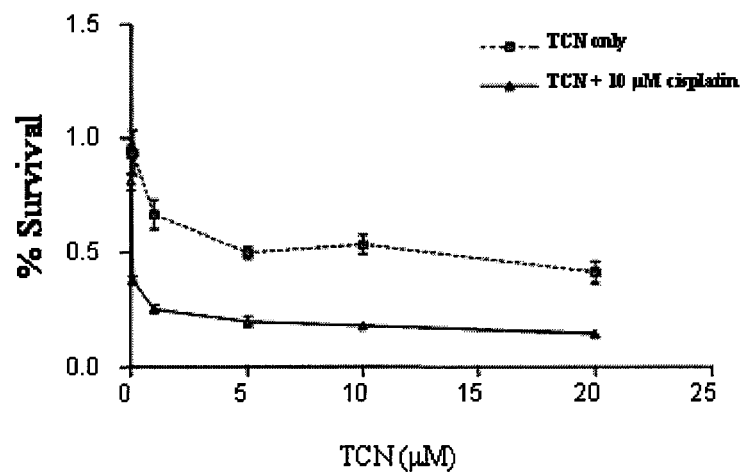
FIG. 16 shows the cell survival of CDDP-resistant cells after treatment. CDDP-resistant ovarian cancer cell line C-13 was treated with API-2 at the indicated concentrations alone or in combination with 10 μM CDDP. 24 hr following treatment, the cells were MTT assayed for cell survival.
Figure 18:
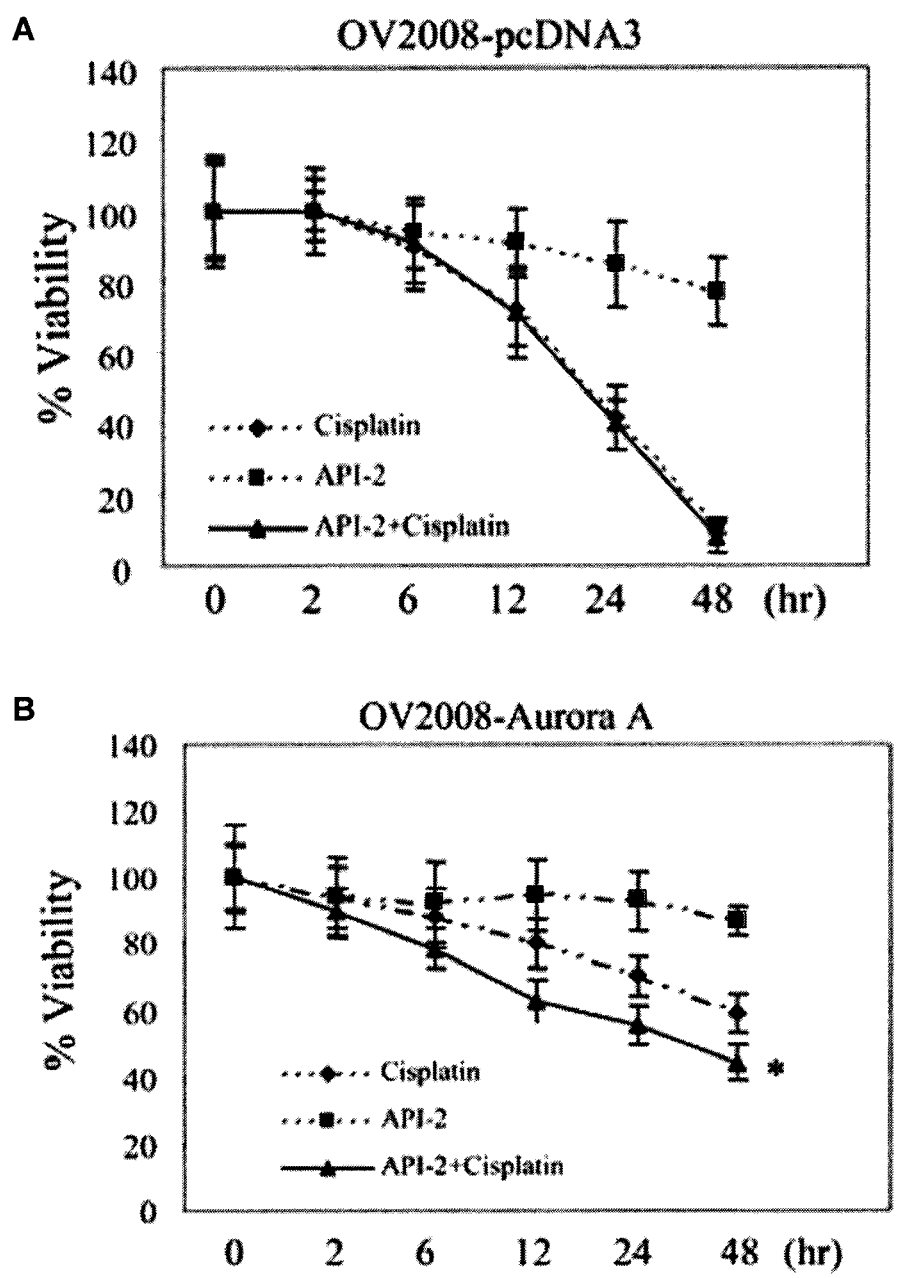
FIG. 18 shows cell survival for CDDP-resistant cells after treatment. CDDP-resistant OV2008 cells were transfected with (A) mock or (B) Aurora-A and grown in 96 well plates. The cells were treated with 10 μM CDDP, 10 μM API-2, or a combination of CDDP and API-2. 24 hr following treatment, the cells were assayed using Capase-Glo™ 3/7.

API-2 was further investigated to determine whether it can overcome CDDP resistance by blocking Akt signaling pathways. A2780CP and C-13 cells were treated with increasing amounts of CDDP alone or in combination with 10 µM API-2. As illustrated in FIG. 15, CDDP alone has no significant effect on cell survival in either cell line. However, cells treated with API-2 and CDDP underwent significant cell death, even at 5-10 µM doses. C-13 cells were treated with varying amounts of API-2 alone or in combination with 10 µM CDDP to determine the effective dosage amounts of TCN and CDDP. 24 hr after treatment, C-13 cell survival was analyzed, with the results illustrating a synergistic or strong cumulative effect with CDDP and low doses of API-2, shown in FIG. 16. The C-13 combination treatment results were confirmed in A2780S and OV2008 cells, as seen in FIGS. 17A and 17B. The combination treatment decreased the survivability of A2780S and OV2008 cells compared to CDDP treatment alone, as shown in FIGS. 18A and 18B.

Figure 19:
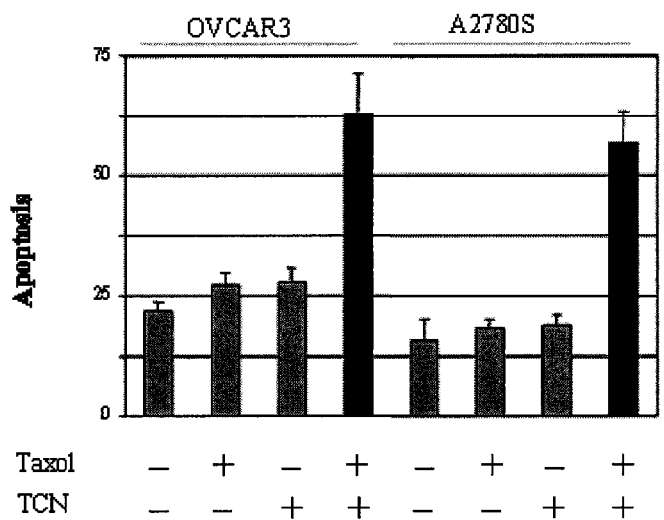
FIG. 19 depicts apoptosis of CDDP-resistant cells after treatment. CDDP-resistant A2780S and OV2008 ovarian cancer cells were treated with 10 μM API-2, 10 μM CDDP, or a combination of the two agents. Cells were assayed by MTT at indicated time points. Each experiment was repeated three times and averaged to obtain the results. P value <0.05.

The effectiveness of TCN combination treatments was determined by treating A2780CP and C-13 cells with TCN, Taxol, or a combination of the two drugs. Apoptosis was determined using Capase-Glo 3/7. Treatment with Taxol or TCN individually increased apoptosis slightly. However, the combination of both drugs significantly increased apoptosis, seen in FIG. 19, indicating a highly synergistic combination treatment between TCN and Taxol.

Figure 20:
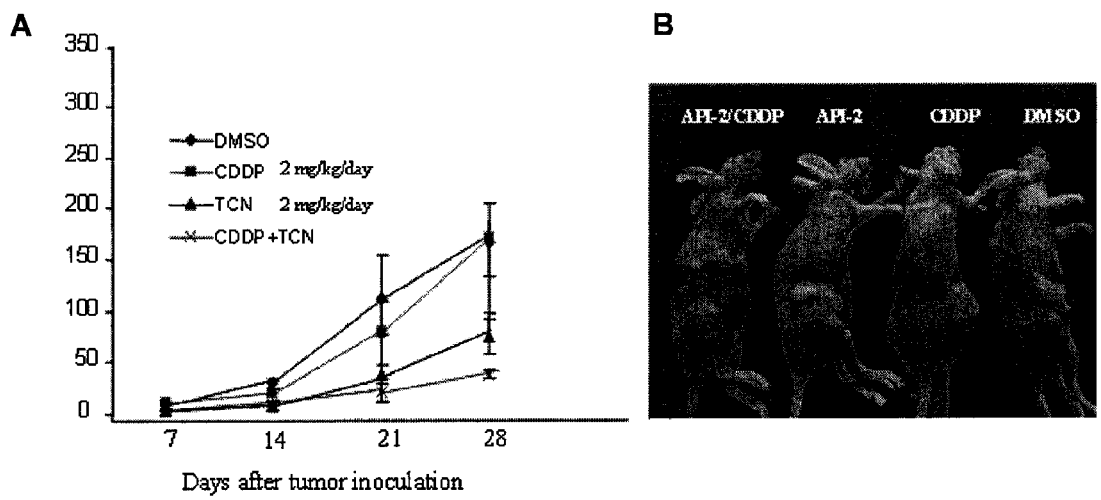
FIG. 20 shows the synergistic effect of combination treatment in inhibiting tumor growth in a xenograft model. C-13 CDDP-resistant cells were subcutaneously injected into nude mice. 7 days after the injection, the mice were treated once a day with 2 mg/kg/day CDDP, 2 mg/kg/day API-2, or a combination of the two agents. (A) Tumor growth curves and (B) tumor size were significantly reduced in mice treated with both API-2 and CDDP, as compared to either agent alone.

The results indicate an additive effect in in vitro systems. To determine the effectiveness of the combination treatment in vivo, C-13 CDDP-resistant cells were injected subcutaneously into nude mice. 7 days following the injection, the mice were treated with CDDP, API-2, or a combination of CDDP and API-2 once a day. Tumor growth curves were calculated at day 7, 14, 21, and 28. After tumor growth was calculated, the mice were sacrificed and tumor size was determined. API-2 effectively reduced both tumor growth and tumor size, but was less effective than the combinatory CDDP/API-2 treatment, as seen in FIGS. 20A and B.

Figure 21:
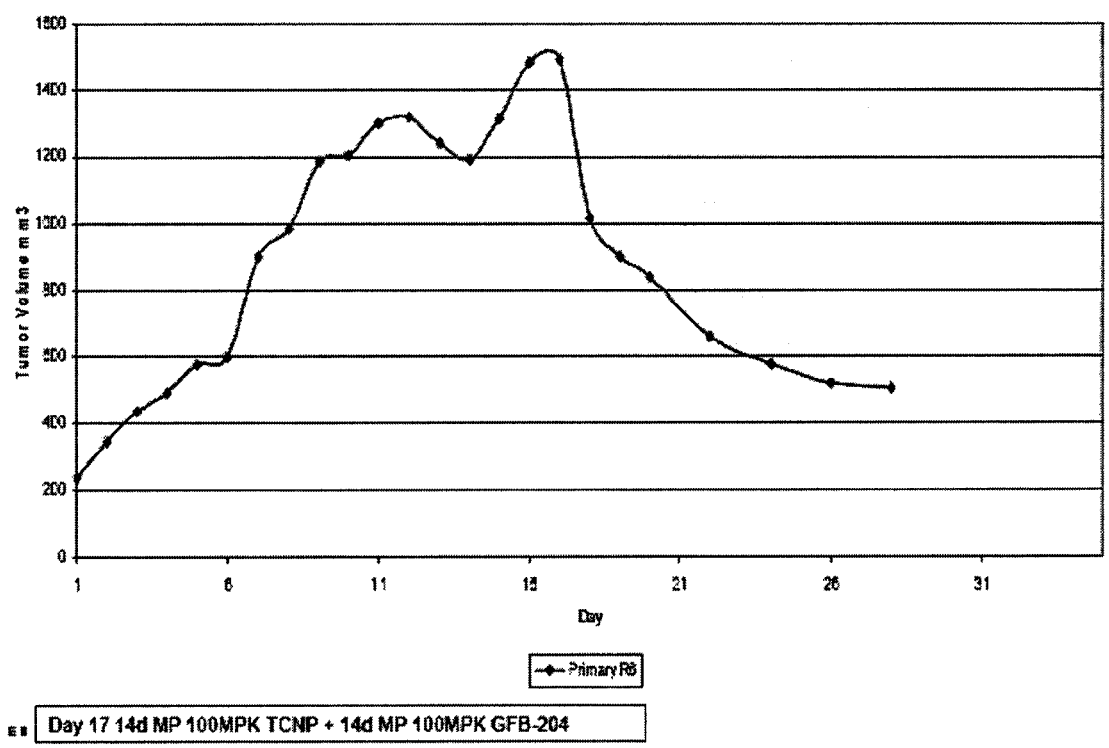
FIG. 21 shows the tumor volume of induced breast cancer in a transgenic model. ErbB2 breast cancer was induced in transgenic mice, then treated with a combination of TCN-P and GFB-204. The treatment induced rapid tumor regression.
Figure 22:
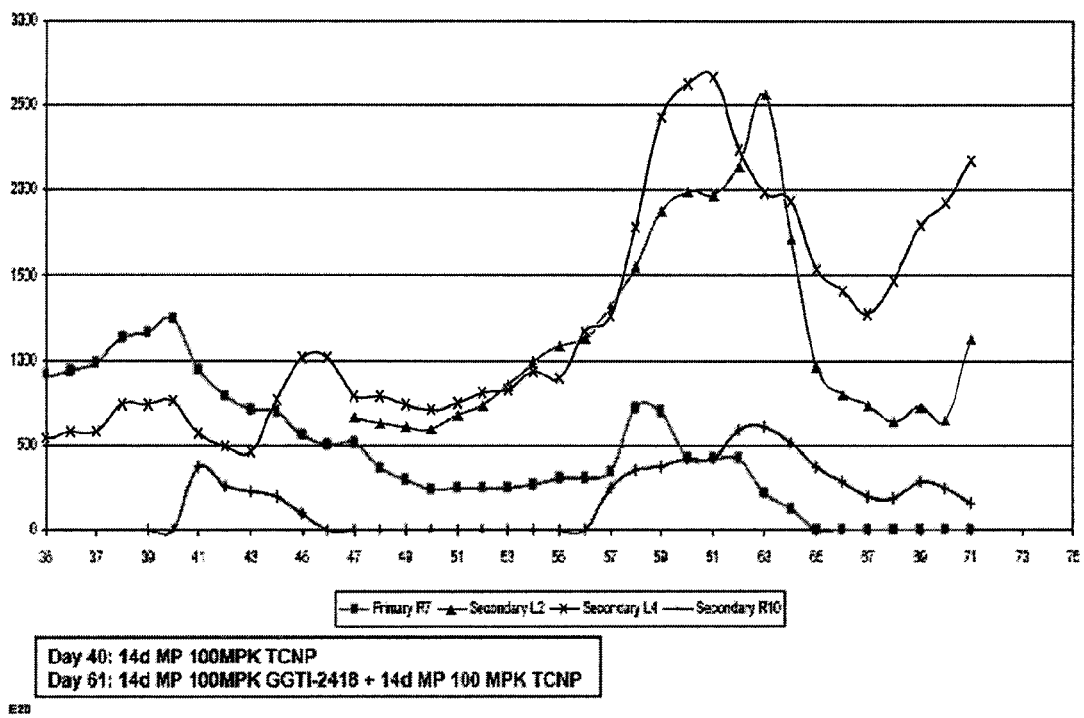
FIG. 22 shows tumor volume of induced breast cancer in a transgenic model. ErbB2 breast cancer was induced in transgenic mice, then treated with a combination of TCN-P and GGTI-2418. The treatment induced rapid tumor regression.

To confirm these results, ErbB2 breast cancer was induced in transgenic mice. 17 days later, the mice were treated with TCNP and GFB-204, a VEGFR and PDGFR tyrosine phosphorylation inhibitor. As seen in FIG. 21, tumor volume decreased rapidly after treatment. The results were replicated using TCNP and GGTI-2418, a geranylgeranyltransferase inhibitor. As with the previous treatment, TCNP and GGTI-2418 resulted in a significant reduction in cancer volume, seen in FIG. 22.

Figure 23:
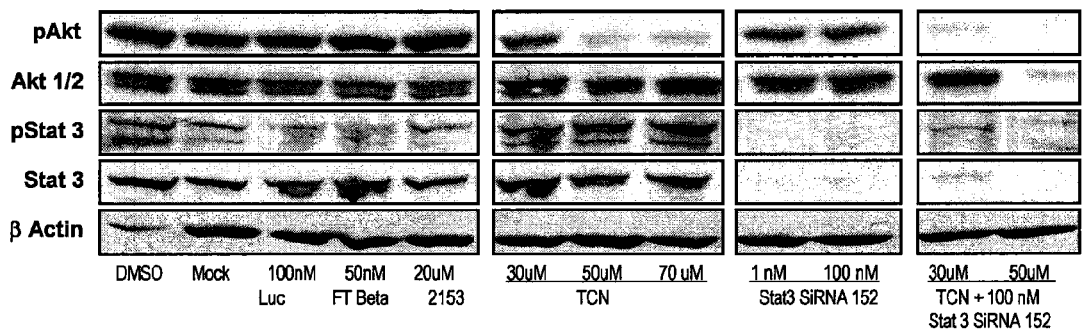
FIG. 23 shows protein levels of cancer cells after combination treatment. MDA-MB-435 cells transfected with Stat3

The effect of TCN with protein knockdown technology was analyzed in breast cancer cell lines. Cells were transfected with siRNA STAT3 and TCN was added to the cell media for 72 hr. In FIG. 23, cell lysates were collected and probed for pAkt, Akt 1/2, pSTAT3, and STAT3. At lower concentrations, the combination treatment removed phosphorylated Akt. However, siRNA STAT3 with higher TCN concentrations, at 50 µM, Akt 1/2 was also not detected, seen in the far right panel of FIG. 23. The cells were also collected to determine proliferation, apoptosis, and cell death, shown in FIG. 24. Additionally, the cells were stained and analyzed with flow cytometry to determine the cell cycle status of the cells. FIG. 25 shows a strong increase in apoptotic cells with a combination treatment of STAT3 siRNA and TCN, compared to TCN alone, confirming the synergistic effect of STAT3 siRNA and TCN.

p53 has been shown to exert tumor suppression by regulating apoptosis, mainly through up-regulation of pro-apoptotic proteins and down-regulation of anti-apoptotic proteins. It has been shown that p53 up-regulates PTEN while reducing PIK3CA expression, leading to inhibition of the Akt pathway. Further, p53 is phosphorylated, and therefore inhibited, by Aurora-A. To test whether Akt could be activated by Aurora-A to mediate a survival signal, cells were transfected with and without Aurora-A. Protein extracts were analyzed, and indicate Aurora-A activation depends on p53, seen in FIGS. 26A though 27B. Akt1 and Akt2 immmunoprecipitates show Akt1 and Akt2 kinase activity and phosphor-S473-Akt were induced by Aurora-A in a dose dependent manner, whereas total Akt levels were unaffected by Aurora-A. Suppression of Aurora-A through RNAi decreased phosphorylation levels of Akt in transfected cells. Also, the addition of Akt inhibitor API-2 abrogated Akt induction by Aurora-A in A2780S and A2780CP cells regardless of whether the cells were transfected with Aurora-A.

The effects of ovarian tumor response were then evaluated with HA-tagged Aurora-A transfected cells, with wild-type or mutant p53. After expression of HA tagged Aurora-A was confirmed by immunoblot, transfected cells were treated with 10 µM CDDP, 100 nM taxol, 5 µM VP16, or 2 µM doxorubicin. MTT analyses at differing times indicate overexpression of Aurora-A significantly reduces CDDP, VP-16, and taxol sensitivity, but has little effect on doxorubicin. However, ectopic expression of Aurora-A has no significant effect on survival of A2780CP cells, seen in FIGS. 28A to 31, implying Aurora-A-induced chemoresistance associates with p53 status. To determine the applicability of the findings to other cells, OV22008 cells with wild-type p53 were transfected with Aurora-A. Upon introduction of Aurora-A, the cells were exposed to CDDP and exhibited reduced cell death, indicating Aurora-A induced CDDP resistance.

To determine the pathway in which Aurora-A induces CDDP resistance, cells were transfected with adenovirus. 48 hours later, the cells were treated with CDDP and cell survival was assayed at various times. Reintroduction of p53 restored CDDP sensitivity in non-Aurora-A-transfected cells, shown in FIGS. 32A to 34 indicating Aurora-A protects cells from CDDP-induced apoptosis through a p53 dependent manner. To further validate Aurora-A's involvement in CDDP resistance, Aurora-A was knocked down using RNAi. Knockdown of Aurora-A enhances CDDP-induced apoptosis and abrogates Aurora-A-induced CDDP resistance, shown in FIGS. 35 through 37B.

A2780CP, A2780S, and OV2008 cells were transfected with Aurora-A or pcDNA3 vector and treated with API-2, CDDP, LY294002 with CDDP, or API-2 with CDDP. Cell viability was calculated at varying time points, showing API-2 alone considerably reduces cell survival in A2780S-Aurora-A, OV2008-Aurora-A and A2780CP cells. Seen in FIG. 38, combination treatment of API-2 with CDDP abrogates Aurora-A-induced CDDP resistance, and reverses phenotypic A2780CP CDDP resistance.

A2780S and A2780CP cell lysates were analyzed for PTEN to prove p53 is required for Aurora-A-induced CDDP resistance. Aurora-A reduces PTEN expression in A2780S, but not A2780CP, cells, as seen in FIGS. 39A to 43. HA-tagged wild-type p53 restores PTEN expression in A2780CP-vector, but not A2780-CP-Aurora-A cells, showing p53 function is abrogated by Aurora-A. Further, ectopic expression of p53 stimulates PTEN promoter activity in A2780CP cells but fails to activate the promoter in Aurora-A cells. Moreover, since Bax is a major target of p53, and is vital in chemotherapeutic agent-induced apoptosis, cell lysates were analyzed for Bax. Following CDDP treatment, cell lysates were immunoprecipitated and immunostained for anti-active Bax antibody. The results show Aurora-A reduces Bax expression and conformational changes, and Bax translocation into the mitochondria.

The effectiveness of TCN with various chemotherapeutics was determined using lung cancer A-549 cells. The cells were treated with varying concentrations of TCN at varying chemotherapeutic agent doses. 72 hr after treatment, cell proliferation and $IC_{50}$ drug effectiveness were analyzed. Further cell lysates were probed for Akt levels and phosphorylation. Combination of TCN with farnesyltransferase inhibitor significantly improves treatment effectiveness, indicating a synergistic effect between TCN and farnesyltransferase inhibitors, as shown in FIGS. 44A through 46B. Further, phosphorylated Akt is severely reduced at low doses of TCN, while total Akt remains unaffected, shown in FIGS. 45 and 47. The results were carried over to other cells lines to test the applicability of combination treatment and reduce cell-specific testing artifacts. Synergistic effects are seen in breast cancer cells, FIGS. 48A through 50B, multiple myeloma cells, FIGS. 52A and 52B, and leukemia cells, FIGS. 53A through 58B. Protein lysates from leukemia cells were collected 24 hr after treatment, and indicate PARP is activated at higher doses of TCN and farnesyltransferase inhibitor, Tipifarnib, as shown in FIGS. 59A and 59B.

The effects of TCN combination treatment were then analyzed in breast cancer cells with 30 µM HER2 inhibitor, Herceptin. Apoptosis and cell proliferation were assayed using trypan blue after 72 hr. As seen in FIGS. 60 and 61, cell death increased slightly with increased TCN dosages. Cell proliferation was drastically reduced at low TCN dosages, but further proliferative inhibition was limited. Additionally, cell lysates were collected and Western blotted for Erb2 and p-Akt, indicating Erb2 and p-Akt levels drop with increasing TCN.

The disclosure of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of treating cisplatin or carboplatin resistant cancer comprising the steps of:
  administering a therapeutically effective amount of a combination of two compounds to a patient having cisplatin or carboplatin resistant cancer, wherein
  a first of the two compounds is an effective dose of cisplatin or carboplatin; and a second of the two compounds being an effective dose of Akt inhibitor, wherein the two compounds act synergistically to induce apoptosis of cancer cells.

2. The method of claim 1 wherein the first of two compounds is cisplatin.

3. The method of claim 1 wherein the Akt inhibitor is Triciribine, Triciribine Phosphate, or API-2.

4. A method of treating cisplatin or carboplatin resistant cancer comprising administering a therapeutically effective amount of a combination of compounds to a patient having cisplatin or carboplatin resistant cancer, wherein:

the first compound is an effective dose of cisplatin; and the second compound is an effective dose of an Akt inhibitor wherein the Akt inhibitor is API-2;

wherein the two compounds act synergistically to induce apoptosis of cancer cells.

5. A method of treating cisplatin or carboplatin resistant cancer comprising administering a therapeutically effective amount of two compounds to a patient having cisplatin or carboplatin resistant cancer, wherein:

the first compound is an effective dose of cisplatin or carboplatin; and the second compound is an effective dose of Triciribine or Triciribine phosphate.

* * * * *

UNITED STATES PATENT AND TRADEMARK OFFICE
CERTIFICATE OF CORRECTION

PATENT NO. : 8,828,451 B2
APPLICATION NO. : 11/867394
DATED : September 9, 2014
INVENTOR(S) : Said M. Sebti et al.

Page 1 of 1

It is certified that error appears in the above-identified patent and that said Letters Patent is hereby corrected as shown below:

In the Specification

Column 1, Line 13 through Line 18 should read:
GOVERNMENT SUPPORT
This invention was made with government support under grant numbers CA067771, CA098473, CA106829, CA107078, CA077935, and CA089242 awarded by the National Institutes of Health. The Government has certain rights in the invention.

Signed and Sealed this
Thirteenth Day of August, 2019

Andrei Iancu
*Director of the United States Patent and Trademark Office*